(12) United States Patent
Douchkov et al.

(10) Patent No.: US 8,222,486 B2
(45) Date of Patent: Jul. 17, 2012

(54) METHOD FOR INCREASING RESISTANCE TO PATHOGENS IN TRANSGENIC PLANTS

(75) Inventors: Dimitar Douchkov, Gatersleben (DE); Patrick Schweizer, Ballenstedt (DE)

(73) Assignee: BASF Plant Science GmbH (DE)

( * ) Notice: Subject to any disclaimer, the term of this patent is extended or adjusted under 35 U.S.C. 154(b) by 508 days.

(21) Appl. No.: 12/438,766

(22) PCT Filed: Aug. 22, 2007

(86) PCT No.: PCT/EP2007/058735
§ 371 (c)(1),
(2), (4) Date: Feb. 25, 2009

(87) PCT Pub. No.: WO2008/025711
PCT Pub. Date: Mar. 6, 2008

(65) Prior Publication Data
US 2010/0011467 A1      Jan. 14, 2010

(30) Foreign Application Priority Data

Aug. 30, 2006  (EP) ..................................... 06119815

(51) Int. Cl.
*C12N 15/09* (2006.01)
*C12N 15/29* (2006.01)
*C12N 15/82* (2006.01)

(52) U.S. Cl. ..... 800/279; 800/306; 800/312; 800/317.2; 800/317.4; 800/320; 800/320.1; 800/320.2; 800/320.3; 800/322; 800/323; 536/23.6; 530/372

(58) Field of Classification Search .................. 800/279, 800/285, 286
See application file for complete search history.

(56) References Cited

U.S. PATENT DOCUMENTS

2004/0123343 A1 *  6/2004  La Rosa et al. ............... 800/278

FOREIGN PATENT DOCUMENTS

WO    WO-99/32619 A1    7/1999

OTHER PUBLICATIONS

Halterman et al. A single-amino acid substitution in the sixth leucine-rich reapeat of barley MLA6 and MLA13 alleviates dependence on RAR1 for disease resistance signaling (2004) Plant J. 38: 215-226.*
Hwang et al. Comparative analysis of evolutionary dynamics of genes encoding leucine-rich repeat receptor-like kinase between rice and *Arabidopsis* (2011) 139: 1023-1032.*
Bieri, S. et al., "RAR1 Positively Controls Steady State Levels of Barley MLA Resistance Proteins and Enables Sufficient MLA6 Accumulation for Effective Resistance", The Plant Cell, (2004), vol. 16, pp. 3480-3495.
Sun, X., et al, "Xa26, a gene conferring resistance to *Xanthomonas oryzae* pv. *oryzae* in rice, encodes an LRR receptor kinase-like protein", The Plant Journal, (2004), vol. 37, pp. 517-527.
"HO30D02w *Hordeum vulgare* cDNA clone HO30D02 3-prime, mRNA sequence", Database EMBL, Accession No. DN186179, Feb. 26, 2005.
Zierold, U., et al., "Transcriptome analysis of *mlo*-mediated resistance in the epidermis of barley", Molecular Plant Pathology, (2005), vol. 6, No. 2, pp. 139-151.
"HO28P17w HO *Hordeum vulgare* cDNA clone HO28P17 3-prime, mRNA sequence", Database EMBL, Accession No. DN186648, Feb. 26, 2005.
Douchkov, D., et al. "A High-Throughput Gene-Silencing System for the Functional Assessment of Defense-Related Genes in Barley Epidermal Cells", Molecular Plant Microbe Interactions, (2005), vol. 18, No. 8, pp. 755-761.
Schweizer, P., et al. "Double-stranded RNA Interferes with gene function at the single-cell level in cereals", The Plant Journal, (2000), vol. 24, No. 6, pp. 895-903.
Rost, B., "Enzyme Function Less Conserved than Anticipated", J. Mol. Biol., vol. 318, (2002), pp. 595-608.

* cited by examiner

*Primary Examiner* — Russell Kallis
*Assistant Examiner* — Steven Bernacki
(74) *Attorney, Agent, or Firm* — Connolly Bove Lodge & Hutz LLP

(57) ABSTRACT

The present invention relates to a method of increasing the pathogen resistance in transgenic plants and/or plant cells, where a DNA sequence which codes for a protein with a leucine-rich-repeat (LRR) domain and/or a kinase activity is introduced into the plant or plant cell and expressed therein. The present invention also relates to the use of nucleic acids which code for such a protein, for the generation of transgenic plants or plant cells with an increased pathogen resistance. The present invention furthermore relates to nucleic acid sequences which code for a protein which confers an increased pathogen resistance in plants.

25 Claims, 1 Drawing Sheet

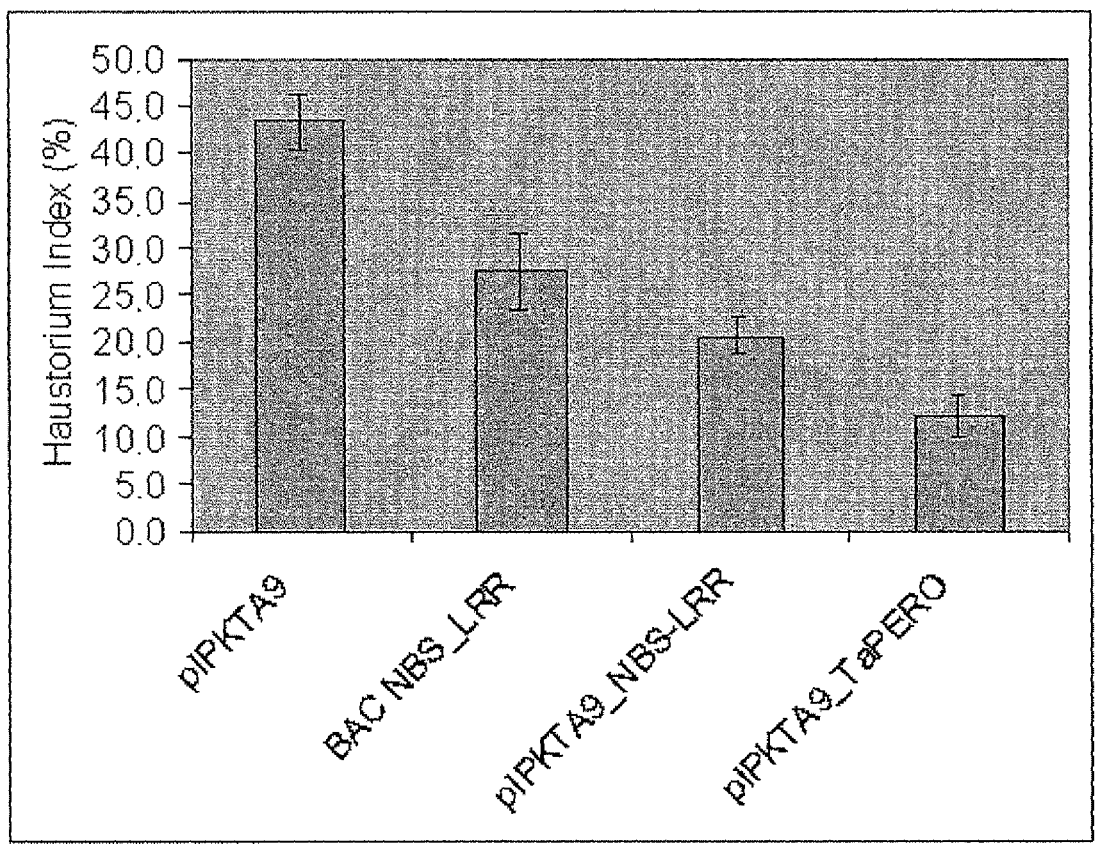

SEQUENCE LISTING

```
<160> NUMBER OF SEQ ID NOS: 10

<210> SEQ ID NO 1
<211> LENGTH: 3277
<212> TYPE: DNA
<213> ORGANISM: Hordeum vulgare
<220> FEATURE:
<221> NAME/KEY: gene
<222> LOCATION: (1)..(3277)
<223> OTHER INFORMATION: spliced genomic sequence of rnr8 gene

<400> SEQUENCE: 1
gaaagatcct gtacttggac tgcatagaaa ggagccaagt cactccactc atcctctcct        60
aagagagacg gacctcgccg ctgccattgc gctccacttg gaacttggag ctggaggaga       120
```

```
gatggggcg cggaggacgc catgcggctg gaggctgctc ttcttccttg ccttgcttct      180
tgccgaggtc cgccatggct cctcttcatc ttcttcaggg gttaaggcgg gagctgctgc      240
tgatgccctc cctcctaggc tctcctctgc tgaagtgcac actcttcgcc ggattgcggc      300
gaatatgggg atatcgcatt ggaacttctc cggcaatccc tgtgaaccca acggcagctt      360
ggtgtgtgac tgctccttca acaacaatac catatgccat gccactgaga tattcctcaa      420
ggaacagaac ttcaccggcc agctcccacc agactttgct gatctccctc atctcctcca      480
gctagaccta agcaggaacg tgttccatgg cacagtgcct gaccggtggg cccggatgag      540
gctgcaagga ctgtcactaa tgggaaacag attgtcaggg ccttttccca tggctcttac      600
gaggatcaca accttgacta gcctgagcat tgaagcaaat gagttccgtg gcaaatccc       660 agcagaaatt gggcatctca cgcaaataga taagctgata atatcaacca acgagttcac      720 tggaccctg ccggctgctc tttccttgct gaccaattta accgacttaa ggatttctgg       780
aaacaattta tctggaaggg ttcctgattt cttggctaaa ctgacaaagc ttgcaaaact      840
gcaaatcgaa ggatctttgc tggaagggcc tattcccctg gcttatcca aattgacaaa       900 cctttctgat ctgaggatta gtgatctgag aggcagtgga tcagcttttcc cggatctaag     960 cagaatgcca tcgatgaaaa cattagtcct caggaattgt tcaatcagcg gaggcatccc     1020
ttcttacata tgggtcatgg aaaatcttaa gcatctggat ctgagctttta atgaactgac    1080 tggaaaagta tcagattcga tcactcttat gggaagcgta gattacatct atctaactgg    1140
aaattcactc actgggaaca tacctgattg gctattggga agcaacagca ttgtgctatc    1200
ttttaataat ttcacgagtg ggagctcagg tcaatgtcaa gggagcgtca atctagtgga    1260
gagttattca cctgaaatga acagtttaaa taatgtccag ccatgcttga agaagaattt    1320
cccatgtgct ttggatggac aatacagatc atccttgcat atcaattgtg gtgacaaaga    1380
agcaatcatc aatggcacaa atacgaagg tgacaccaca ccaaaaggtg cttccgtgtt     1440
gtatgtaagc ccagactcaa actgggcatt cagcagcact gggaacttca tggacaacaa    1500
catcaatgat gacaaataca ttgcgtcaag cacatcaaaa ctgacaatgc ccgactcaaa    1560
gttgtatgca agagcacgcc tttctcctct ttcgctcaca tattacgggc gttgcatgca    1620
taatgggagc tacacagtta aactccattt tgccgaaatt atattcacca atgacagtac    1680
atactgcagc cttggcaaaa gaaaattcaa tgtgttcata cagggaagaa tggtgctaga    1740
ggattttgat attgagcaat ctgctggtgg ggctggaaag ccagtcatca aggcttttcaa   1800 aacatatgtc acaaatcata cactgaagat tcaattctat tgggcaggaa gagggacaac    1860
aggcattcca gatagagtat tttacggccc tctagtatct gcaatatcag taaatccaaa    1920
cttccaaatt cctttggctg ttgaacctcc ccatactggc agtggcacaa aaacttcaag    1980
gacagctaaa gctttgctga ttggagcccc aattattgcg atattcactg ctcttattgt    2040
tggcatctac tggattaggc ggcgacggaa gaacttggtg aatcaagatc tccgggcact    2100
tgacctccaa attggctcat ttaccttgag acaaatcaaa gcagcgacta ggaactttga    2160
tccagcgaac aagattggcg aaggtggttt tggttcggtt tacaagggtt tgttgtccga    2220
tggcaccatt attgctgtca acagctatc atcgaagtcc aagcaaggga atcgtgaatt     2280
tgtgaatgag ataggcatga tatctgcact ccagcatcca aaccttgtca ggttgtatgg    2340
ctgttgtaca gaaggaaacc agctattgct agtttacgag tacatggaaa ataattgcct    2400
tgcacgtgct ctatttgttg aagaatatag actggcattg gattggccaa caagacgtaa    2460
gatttgcctg ggaatagcaa ggggtctggc atatatgcat gaggagtctg caataaggat    2520
```

```
tgtgcaccga gatatcaagg ctagcaatat actgcttgac aaagatttgg atgctaagat    2580
ctcagatttt ggtctagcaa agcttaatga agatggtcac acccacataa gcacgaaagt    2640
agctggaact attggataca tggctcctga gtacgcaatg cgtggttatt tgacagacaa    2700
agctgatgtt tacagttttg gggttgttgc tttggaaatt gtgagtggaa aaagcaacac    2760
aaactacagg ccaaaggaag attttgttta tcttctcgat tgggcttgtg ttttacatga    2820
gagaggaact ctactggagc tggtagatcc agacttagga tccaattact caacggaaga    2880
ggcactcctg atgctgaacg tggctctctt atgcaccaac gcagcaccga ctcttagacc    2940
aaagatgtcc aacgctgtga gccttcttga aggccatacc cccctgcaac ccttcctatc    3000
agaactcagc cttgctgcaa acagcctgag ctcaagtggt ctacgcagaa acttctggga    3060
aaatccaagt gagagccaga gcataacggc acaagcatca tataacaaca ccagtgactc    3120
gtcatcttta gatgtagatg gtagcttgag acattctgcg acttaaatgt tagatgtatt    3180
tcagatctgt acacctgtaa gaataactag ggctatgcca ctatgtctat tctggcagta    3240
caatgtagct actaacataa aaacacctaa ttctact                              3277
```

<210> SEQ ID NO 2
<211> LENGTH: 1014
<212> TYPE: PRT
<213> ORGANISM: Hordeum vulgare
<220> FEATURE:
<221> NAME/KEY: misc_feature
<223> OTHER INFORMATION: Rnr8 protein sequence

<400> SEQUENCE: 2

```
Met Gly Ala Arg Arg Thr Pro Cys Gly Trp Arg Leu Leu Phe Phe Leu
1               5                   10                  15

Ala Leu Leu Ala Glu Val Arg His Gly Ser Ser Ser Ser Ser Ser Ser
            20                  25                  30

Gly Val Lys Ala Gly Ala Ala Asp Ala Leu Pro Pro Arg Leu Ser
        35                  40                  45

Ser Ala Glu Val His Thr Leu Arg Arg Ile Ala Ala Asn Met Gly Ile
50                  55                  60

Ser His Trp Asn Phe Ser Gly Asn Pro Cys Glu Pro Asn Gly Ser Leu
65                  70                  75                  80

Val Cys Asp Cys Ser Phe Asn Asn Asn Thr Ile Cys His Ala Thr Glu
                85                  90                  95

Ile Phe Leu Lys Glu Gln Asn Phe Thr Gly Gln Leu Pro Pro Asp Phe
            100                 105                 110

Ala Asp Leu Pro His Leu Leu Gln Leu Asp Leu Ser Arg Asn Val Phe
        115                 120                 125

His Gly Thr Val Pro Asp Arg Trp Ala Arg Met Arg Leu Gln Gly Leu
130                 135                 140

Ser Leu Met Gly Asn Arg Leu Ser Gly Pro Phe Pro Met Ala Leu Thr
145                 150                 155                 160

Arg Ile Thr Thr Leu Thr Ser Leu Ser Ile Glu Ala Asn Glu Phe Arg
                165                 170                 175

Gly Gln Ile Pro Ala Glu Ile Gly His Leu Thr Gln Ile Asp Lys Leu
            180                 185                 190

Ile Ile Ser Thr Asn Glu Phe Thr Gly Pro Leu Pro Ala Ala Leu Ser
        195                 200                 205

Leu Leu Thr Asn Leu Thr Asp Leu Arg Ile Ser Gly Asn Asn Leu Ser
210                 215                 220
```

```
Gly Arg Val Pro Asp Phe Leu Ala Lys Leu Thr Lys Leu Ala Lys Leu
225                 230                 235                 240

Gln Ile Glu Gly Ser Leu Leu Glu Gly Pro Ile Pro Leu Gly Leu Ser
            245                 250                 255

Lys Leu Thr Asn Leu Ser Asp Leu Arg Ile Ser Asp Leu Arg Gly Ser
                260                 265                 270

Gly Ser Ala Phe Pro Asp Leu Ser Arg Met Pro Ser Met Lys Thr Leu
        275                 280                 285

Val Leu Arg Asn Cys Ser Ile Ser Gly Gly Ile Pro Ser Tyr Ile Trp
    290                 295                 300

Val Met Glu Asn Leu Lys His Leu Asp Leu Ser Phe Asn Glu Leu Thr
305                 310                 315                 320

Gly Lys Val Ser Asp Ser Ile Thr Leu Met Gly Ser Val Asp Tyr Ile
                325                 330                 335

Tyr Leu Thr Gly Asn Ser Leu Thr Gly Asn Ile Pro Asp Trp Leu Leu
            340                 345                 350

Gly Ser Asn Ser Ile Val Leu Ser Phe Asn Asn Phe Thr Ser Gly Ser
        355                 360                 365

Ser Gly Gln Cys Gln Gly Ser Val Asn Leu Val Glu Ser Tyr Ser Pro
370                 375                 380

Glu Met Asn Ser Leu Asn Asn Val Gln Pro Cys Leu Lys Lys Asn Phe
385                 390                 395                 400

Pro Cys Ala Leu Asp Gly Gln Tyr Arg Ser Ser Leu His Ile Asn Cys
                405                 410                 415

Gly Asp Lys Glu Ala Ile Ile Asn Gly Thr Lys Tyr Glu Gly Asp Thr
            420                 425                 430

Thr Pro Lys Gly Ala Ser Val Leu Tyr Val Ser Pro Asp Ser Asn Trp
        435                 440                 445

Ala Phe Ser Ser Thr Gly Asn Phe Met Asp Asn Asn Ile Asn Asp Asp
    450                 455                 460

Lys Tyr Ile Ala Ser Ser Thr Ser Lys Leu Thr Met Pro Asp Ser Lys
465                 470                 475                 480

Leu Tyr Ala Arg Ala Arg Leu Ser Pro Leu Ser Leu Thr Tyr Tyr Gly
                485                 490                 495

Arg Cys Met His Asn Gly Ser Tyr Thr Val Lys Leu His Phe Ala Glu
            500                 505                 510

Ile Ile Phe Thr Asn Asp Ser Thr Tyr Cys Ser Leu Gly Lys Arg Lys
        515                 520                 525

Phe Asn Val Phe Ile Gln Gly Arg Met Val Leu Glu Asp Phe Asp Ile
    530                 535                 540

Glu Gln Ser Ala Gly Gly Ala Gly Lys Pro Val Ile Lys Ala Phe Lys
545                 550                 555                 560

Thr Tyr Val Thr Asn His Thr Leu Lys Ile Gln Phe Tyr Trp Ala Gly
                565                 570                 575

Arg Gly Thr Thr Gly Ile Pro Asp Arg Val Phe Tyr Gly Pro Leu Val
            580                 585                 590

Ser Ala Ile Ser Val Asn Pro Asn Phe Gln Ile Pro Leu Ala Val Glu
        595                 600                 605

Pro Pro His Thr Gly Ser Gly Thr Lys Thr Ser Arg Thr Ala Lys Ala
    610                 615                 620

Leu Leu Ile Gly Ala Pro Ile Ile Ala Ile Phe Thr Ala Leu Ile Val
625                 630                 635                 640

Gly Ile Tyr Trp Ile Arg Arg Arg Lys Asn Leu Val Asn Gln Asp
                645                 650                 655
```

Leu Arg Ala Leu Asp Leu Gln Ile Gly Ser Phe Thr Leu Arg Gln Ile
        660                 665                 670

Lys Ala Ala Thr Arg Asn Phe Asp Pro Ala Asn Lys Ile Gly Glu Gly
675                 680                 685

Gly Phe Gly Ser Val Tyr Lys Gly Leu Leu Ser Asp Gly Thr Ile Ile
        690                 695                 700

Ala Val Lys Gln Leu Ser Ser Lys Ser Lys Gln Gly Asn Arg Glu Phe
705                 710                 715                 720

Val Asn Glu Ile Gly Met Ile Ser Ala Leu Gln His Pro Asn Leu Val
                725                 730                 735

Arg Leu Tyr Gly Cys Cys Thr Glu Gly Asn Gln Leu Leu Val Tyr
        740                 745                 750

Glu Tyr Met Glu Asn Asn Cys Leu Ala Arg Ala Leu Phe Val Glu Glu
        755                 760                 765

Tyr Arg Leu Ala Leu Asp Trp Pro Thr Arg Arg Lys Ile Cys Leu Gly
770                 775                 780

Ile Ala Arg Gly Leu Ala Tyr Met His Glu Glu Ser Ala Ile Arg Ile
785                 790                 795                 800

Val His Arg Asp Ile Lys Ala Ser Asn Ile Leu Leu Asp Lys Asp Leu
                805                 810                 815

Asp Ala Lys Ile Ser Asp Phe Gly Leu Ala Lys Leu Asn Glu Asp Gly
            820                 825                 830

His Thr His Ile Ser Thr Lys Val Ala Gly Thr Ile Gly Tyr Met Ala
        835                 840                 845

Pro Glu Tyr Ala Met Arg Gly Tyr Leu Thr Asp Lys Ala Asp Val Tyr
850                 855                 860

Ser Phe Gly Val Val Ala Leu Glu Ile Val Ser Gly Lys Ser Asn Thr
865                 870                 875                 880

Asn Tyr Arg Pro Lys Glu Asp Phe Val Tyr Leu Leu Asp Trp Ala Cys
            885                 890                 895

Val Leu His Glu Arg Gly Thr Leu Leu Glu Leu Val Asp Pro Asp Leu
        900                 905                 910

Gly Ser Asn Tyr Ser Thr Glu Glu Ala Leu Leu Met Leu Asn Val Ala
        915                 920                 925

Leu Leu Cys Thr Asn Ala Ala Pro Thr Leu Arg Pro Lys Met Ser Asn
930                 935                 940

Ala Val Ser Leu Leu Glu Gly His Thr Pro Leu Gln Pro Phe Leu Ser
945                 950                 955                 960

Glu Leu Ser Leu Ala Ala Asn Ser Leu Ser Ser Gly Leu Arg Arg
                965                 970                 975

Asn Phe Trp Glu Asn Pro Ser Glu Ser Gln Ser Ile Thr Ala Gln Ala
        980                 985                 990

Ser Tyr Asn Asn Thr Ser Asp Ser  Ser Ser Leu Asp Val  Asp Gly Ser
        995                 1000                1005

Leu Arg  His Ser Ala Thr
    1010

<210> SEQ ID NO 3
<211> LENGTH: 10626
<212> TYPE: DNA
<213> ORGANISM: Hordeum vulgare
<220> FEATURE:
<221> NAME/KEY: gene
<222> LOCATION: (1)..(10626)
<223> OTHER INFORMATION: genomic sequence of rnr8 gene

```
<400> SEQUENCE: 3
agaaagatcc tgtacttgga ctgcatagaa aggagccaag tcactccact catcctctcc      60
taagagagac ggacctcgcc gctgccattg cgctccactt ggaacttgga gctggaggag     120 agatggggc gcggaggacg ccatgcggct ggaggctgct cttcttcctt gccttgcttc     180
ttgccgaggt ccgccatggc tcctcttcat cttcttcagg ggttaaggcg ggagctgctg     240
ctgatgccct ccctcctagg ctctcctctg ctgaaggtat gtgtgtgtgc tcagcacctg     300
caaatgcatt gctctatctc tgccatcggg tgattcccct ctcctctgcg tttggctcaa     360
tggttcggaa acatatatga ctctgataag cagagcgtga tttcttttgg cttccaaggc     420 ttgattttc tcctctttct ccttctttcc cctttcgtc tcctttgctt ctcccatttt     480
tggtcttctt tgcttgggc cgtcgaggag gagccagaac agtactgcaa aaagaacgaa     540
ccaatgacaa aaaaaactc tctaaacaag agagcaagat cgagaatctt ggatatattt     600
tcttccaaag gaatgcaaac ccgccgcgtt catgttttt ttttccttt tgccattctc     660 gtagtgcaca ctcttcgccg gattgcggcg aatatgggga tatcgcattg gaacttctcc     720
ggcaatccct gtgaacccaa cggcagcttg gtgtgtgact gctccttcaa caacaatacc     780
atatgccatg ccactgagat gtatgtatgc ataactcctt ggcgcttctc gtaaaacatt     840
gggggaaacc tgtaaaattg atcttactac tagagtagaa ctgagcagat catgttcgtg     900
catttctgtg ctctaacatg tgctacctgt tgcactgttc ttccgatcat ctttgcagat     960
tcctcaagga acagaacttc accggccagc tcccaccaga ctttgctgat ctccctcatc    1020
tcctccagct gtaagtacta acagccagt caaactaatt taagccttgt tcagaaaaaa    1080
taatctaact ttaggtgttt ctcaagataa tactaacacc ataattccgc attacaatgt    1140
tgcagagacc taagcaggaa cgtgttccat ggcacagtgc ctgaccggtg ggcccggatg    1200
aggctgcaag gactgtgagt ggcctcgccc ttcaccttac ccattgttat ctttgagtga    1260
gtagtacagc aaaatgtagc atgtggagct attttggact ctatccaaga acaatatgcc    1320
actaaaaaga tatatatttt gggcggaact ggtgaaggca cagtccctat ctatggagca    1380
tgactgcaat gtcggcatgc caaagcatct cagaaggcaa caaattaggc tactcccaag    1440
cacgattttc aaaatgccag gcatctttg tgcagtgctc taccaacctt tttagcagtg    1500
cagaatatag tctagcatga atccatgaag aataaaatca agcaataagc agcattttcc    1560
gcgccgctgt cttgtcgatg cgatattaaa attgctacta tttctaacca ggccataggg    1620
gagatgagat ctatgacaat gcccttaat tcatgacaaa ctagttacga tttctcttatg    1680 agaagggcat tgcatcatta ccacttgacc gtgttggata tcgctaaccg gatgttcctt    1740
ggatgggcaa acatggctgt agcaaataac tgcacccaga atgacagtag agctgcactg    1800
cagaaaccag ggttgcaatg tattagtaaa aaaaatgttc gagacatatt taattgcaac    1860
atattgctaa gaaaatttac aagtcatatt taagcctaaa tctgtgtgct tcgtttattg    1920
gcttccagtc agaatactgt tgcaaaagag ttcaatttag agtgtccctt gcctgattgc    1980
ctccttggag ctcagtctcc catgtctgga aagaggatat cattccggga gtgactaagc    2040
actgtgtctg tgtggatgtt ctgccagcac gccctagatt ctagttgggg acctcagtaa    2100
tgaactccca tttgtctcat ataggaagaa ctcgccatgt tttgttatca gaaaatcta    2160 ttgccatgtt ctcccatcgc aagaaaaaaa gaactcttca taaaaccttca cattttccat    2220 gtctgaagaa aaatacgagc acaagcttag aatgattcaa gttccagttt agttatactc    2280
ccttcatttc atttacgaga catggtttag tatagcacgg aaattattcc ccaaaattat    2340
```

-continued

```
actctctccg tttcataata taagtctttt tagagatttc actagaggac tacatacgga      2400
tgtatataga catactttaa agtgtagatt cattcatttt actttgtatg tagtccctta      2460
gtgaaatcgc ttaaaagact tatatttagg aacaagggga gtattaaaaa agcttgttta      2520
gtcataaacg ataaagggtt tcccctcgct ttatattata aagcaaccat tcgatacatc      2580
cagcttgctg gagccgcagc acaaacaaac ccaaaaagaa aaacgagac aaagaaagag       2640 aaacaaatgc cgacaccgac agatcaatga agcaaaaatg ccggcaacc gctgcaccct       2700 ccggagaagt tgcaccgcgc tcctagcact ctaaagcgtc gcatgacccg cggcgccgg       2760 caggcgtcgc cgcgttggag ccggacgagc cgccaaggat ttctctcgac ccaaaccccc      2820
accaccacct cagatgatcc aaagtgcacc aaccaacttg ccgcccacca gcccgtgcca      2880
ccacggtcac tgaaccaact ttgtcgtctt actgaggcca ccgacatgaa acctggagga      2940
cagaagaaaa gacgatgggc tcgggggcat ccgtgacata gccgacacga ggggacatcc      3000
tccaccgccg ccgcggagcc gatccgacgc agcgacaggg gcctacaggc actgatggct      3060
cgaacggatc caaaagggtc cggatagccc ctgccgccac gctgcagctc gtcagccgac      3120
gaagccgcca ccgctcgtag atcaccgcct cctcgccacc atcaccaggg agcagcgccg      3180
ccgcgcgtcg agccgccagc ccgccccagc ccagaaagag cccgaaaagg cctagatctg      3240
ggccgggcca ccagcaccac cacaccgtcc cacggccaac agccgcactg ccgcatcaag      3300
ggcacccgag gcccgcggga accccgccac cgagccacac cgccaccacc atcgggaggc      3360
tcccacgccc ctctacgcgt gcggggagga agaacggccc gtcgccgcca gcgccccgcg      3420
ggcagggccc gacggaccat gccaccgccg gcgggagggg agaacgacgg ggagggtgct      3480
ggaggagagg gggatcaggg ggttcgcccg tcgcccgcgg ggaagcgagc gagcgaacca      3540
acgagaagtg gagttccggt ttttgtttag tcataaacga caagtaaatt gaggaacaga      3600
gaaaaatcat tgaataacta gactggacaa gcatgcaata atgtgaaata ctcttatgaa      3660
acaaatttct acttgttccc tgtgataaga atttcaatta ttttccgcgtt ttaagccaca     3720 aaattttgca taattgtaag aaatggaatg ccgtaaaaca gaattatgca gcgtgtcatt      3780
gatctgttca tgccaaagtc ctgcaggtca ctaatgggaa acagattgtc agggccttt      3840 cccatggctc ttacgaggat cacaaccttg actagcctgt aagcaagaaa tttggtgaaa      3900
acaactttga tttcctactt ttgagttctc ttttctaact acaatctgaa ataataatc       3960 cgaaggagca ttgaagcaaa tgagttccgt gggcaaatcc cagcagaaat tgggcatctc      4020
acgcaaatag ataagctgtg agtattttgc tttgcctaca ttgcttgtac aacagacaag      4080
agttgcaggt atttggttaa catagttcct tatgacctat acactgatct tgctcagga      4140 taatatcaac caacgagttc actggacccc tgccggctgc tctttccttg ctgaccaatt      4200
taaccgactt gtaaggattc tacgatcttt gttttttccct gtagccctct gcagactctt      4260
tttgtaatgt tcggctattg aatctcctaa cagaaggatt tctggaaaca atttatctgg      4320
aagggttcct gatttcttgg ctaaactgac aaagcttgca aaactgtaag ttggagagtt      4380
catggcagaa cagattacaa atccacagat acccaagtat ataatttatt aaagggatt      4440 tctcacgatg caggcaaatc gaaggatctt tgctggaagg gcctattccc ctgggcttat      4500
ccaaattgac aaacctttct gatctgtacg atgacaaatg tttgagatac tcaattctag      4560
ctgcaccatc caattttattt attggattga agtgttaaac taaagcggga aattctggtt      4620 gcgtcttttct gttaaccagg aggattagtg atctgagagg cagtggatca gctttcccgg      4680
atctaagcag aatgccatcg atgaaaacat tgtaagttat aatctgctga gttcccgtgc      4740
```

```
tttttgtata taggttctca tataatatga acttttttaaa tgtagagtcc tcaggaattg    4800
ttcaatcagc ggaggcatcc cttcttacat atgggtcatg gaaaatctta agcatctgta    4860
agttcatcgc attggttcca tatagactat agaacaatgc agtgtgttgg gagtacacat    4920
aaaatatgtc agagctgaat gtactcggtg ttgacatgtt tttatcatca atgttctcta    4980
tgcagggatc tgagctttaa tgaactgact ggaaaagtat cagattcgat cactcttatg    5040
ggaagcgtag attacatgta agttggtatt tataataaat tgtactaggc atgctatttt    5100
attgggctac tttcctgaat gcacctcaac aaaaacaatc ttgcagctat ctaactggaa    5160
attcactcac tgggaacata cctgattggc tattgggaag caacagcatt gtgtaagttc    5220
gtgtgtacat gcactctcca gagatgcatc attcttagat gctaatactt atagatattc    5280
atgacttcct atcacatttt ttcctttttcc cgaatctttt aaaagctgtc ataaaagtgc    5340
agaacatatg agttaacata tctaagatat aaagtgttat taggtgtcaa tacccaattc    5400
attcatgacg ggagaaaacc tataagatga tgttcttgat cacaagcatc cagagttagc    5460
atttccttaa aaactatttta ggcatgcctc tatctgctcc gtctgctaaa caggcatgcc    5520
tctatctgct ctgtctatta ataattatg ttggctgcat aacagaatag ctcatgccca    5580
tatgtacatg aaacttagag cttaagagaa tgtagtatga ctgctagtgc tatgattgaa    5640
tctctaacag tctgaactaa aaaaaatgca tttcttactt gatgtactta aatttactat    5700
gaaactatca aatgcaggga cctatctttt aataatttca cgagtgggag ctcaggtcaa    5760
tgtcaaggga gcgtgtaaga aagctgtatc agaattctg agtttttctc cgtgacaacg    5820
attgtgcaaa taattaaata gtttcctatg attcttcaaa ttgcagcaat ctagtggaga    5880
gttattcacc tgaaatgaac agtttgtaag attctttatc ctgttgcttc aaaagattaa    5940
agagctttcg accaacagag aaatccagac ataataacct cttattttac tctcggtgat    6000 tctaccttc tgtgcagaaa taatgtccag ccatgcttga agaagaattt cccatgtgct    6060
ttggatggac aatgtaagtt gacgcccagt attttgttttg tcactgttgc ttctgatcac    6120
cactgaatgg gaaaaacaaa ataacagatg tttgttgacg cttttcatac ccgtgctcat    6180
gattgtgaca aacaagacta gctttaccaa tgaatcagaa gaagttacaa attgatattt    6240
ctggattgta aaattatcag gataaactct aaaaaacaca agcaacaaga taactcacaa    6300
ggatataatt agatcctgtg caaaagttca ttggtgctaa gcacacaagc caaacttttt    6360 tttttcttgaa cacagaagcc aaacagaaaa gatcattgaa gctgtatgta atgatgttat    6420
atgcattttc acagacagat catccttgca tatcaattgt ggtgacaaag aagcaatcat    6480
caatggcaca aaatacgaag gtgacaccac accaaaaggt gcttccgtgt tgtatgtaag    6540
cccagactca aactgggcat tcagcagcac tgggaacttc atggacaaca acatcaatga    6600
tgacaaatac attgcgtcaa gcacatcaaa actgacaatg cccgactcaa agttgtatgc    6660
aagagcacgc ctttctcctc tttcgctcac atattacggg cgttgcatgc ataatgggag    6720
ctacacagtt aaactccatt tgccgaaaat tatattcacc aatgacagta catactgcag    6780
ccttggcaaa agaaaattca atgtgttcat acaggtatga ccagataaga aaatattcgg    6840
tcatttacat tttaataata gctgtatctt gttagctcct gtgatagtaa caagatactg    6900
tatgatctca gggaagaatg gtgctagagg attttgatat tgagcaatct gctggtgggg    6960
ctggaaagcc agtcatcaag gctttcaaaa catatgtcac aaatcataca ctgaagattc    7020
aattctattg ggcaggaaga gggacaacag gcattccaga tagaggattt tacggccctc    7080
tagtatctgc aatatcagta aatccaagta tgtcattttt aacacattat ttctgaattt    7140
```

```
tgcataatgt gctccattaa tcactgtggg aagggtacat catttaacaa ggaacagcac    7200
atgacggcat cttctgactt cttgcattac agttttgacg gagaaatact ctattcttta    7260
atgatctggt gattttggtt tatgtttgtt catactcaga cttccaaatt cctttggctg    7320
ttgaacctcc ccatactggc agtggcacaa aaacttcaag gacagctaaa gctttgctga    7380
ttggagcccc aattattgcg atattcactg ctcttattgt tggcatctac tggattaggc    7440
ggcgacggaa gaacttggtg aatcaaggtg ctataaatat tttttaatca acttttttt    7500 ttatttatac ctccaatggc aaggacaggc ctggtgcagt ggtgaagtac tccccacttg    7560
tgccaagagg tcctgggttc gacgtggcct ctctgcattg cactgtgcag gggtaaggct    7620
tgcctcgtat aatccttccc cagatcccgc ctggtgtggg agcttctagc actgggtctg    7680
tcctttacac cgtcaatgat aactggtgct tatctttcac tttgcttcac cgttcataca    7740
caccatctat agcatccctc tactttccac ttctcagcag aacaagcaat agcaagatga    7800
ctactatata gcaatgtaaa cctagtgaaa atcataatca tcaactatac gttctgaata    7860
tttctgaccc atatgataac ttttattaga tctccgggca cttgacctcc aaattggctc    7920
atttaccttg agacaaatca aagcagcgac taggaacttt gatccagcga acaagattgg    7980
cgaaggtggt tttggttcgg tttacaaggt cagtcttcac tctctcccat gcttaaattc    8040
tacaaactga agttaaatta catgattctt acaacgaaat aatgtttgtg ctagcagggt    8100
ttgttgtccg atggcaccat tattgctgtc aaacagctat catcgaagtc caagcaaggg    8160
aatcgtgaat ttgtgaatga gataggcatg atatctgcac tccagcatcc aaaccttgtc    8220
aggttgtatg gctgttgtac agaaggaaac cagctattgc tagtttacga gtacatggaa    8280
aataattgcc ttgcacgtgc tctatttggt aatcaatact tctatatttc ttggtgctcc    8340
ccctaactag tattgcatgt taatcatgaa taatttgtat tgtgcggtcc agttgaagaa    8400
tatagactgg cattggattg gccaacaaga cgtaagattt gcctgggaat agcaaggggt    8460
ctggcatata tgcatgagga gtctgcaata aggattgtgc accagatat caaggctagc    8520 aatatactgc ttgacaaaga tttgatgct aagatctcag attttggtct agcaaagctt    8580
aatgaagatg gtcacaccca cataagcacg aaagtagctg gaactatgta agtactttca    8640
attatgtatt ttttccgaa atgcaaaatt ctatccacac attcccattt gatctatata    8700
acaaaaagat aagaaggaaa agcagttaaa aggaaagtac tgcctctgta acttttata    8760 ggacgttttt agagtcaatg acagtgtcaa aaaacgtctt atattaagtt acagagggag    8820
taatagtgca gtgatgaaca atactccctc cgtctctatt tacatggcgt ccttgttttt    8880
ttgtgatttc actttgaaca taatttggcc aattgataca ttaggaactt tttcgaatat    8940
gagttcaatg gtatgatttt tatggcacat aaccacggt tcgttggtca aattgatggt    9000
caaggttgga tcttgaaatg tgtgggcatc atgtaaacag ggacggaggg agtataacat    9060
ttacctccgg caaaaataca gaacatccat atagagataa aagttaacat caggtaagct    9120
ggtcagaaac ccgcataaat gtagcacctt ggctttcctg catacaaaca taaattacaa    9180
aaaaatgcaa tcaactttag attaacattt tccatgcaat gggatgctta aaaggtgttc    9240
taattttcat tcaaacaact acggatggat attactttc ggcatatctt tctaagtaat    9300
tcctttagct gcgcagttta cagctgattt gattatttta tcattcttgc agtggataca    9360
tggctcctga gtacgcaatg cgtggttatt tgacagacaa agctgatgtt tacagttttg    9420
gggttgttgc tttggaaatt gtgagtggaa aaagcaacac aaaactacagg ccaaaggaag    9480 attttgttta tcttctcgat tgggtaactt ataaaccttc gtacccctct tgcagtaata    9540
```

```
tggaccatac tgaatagact aatatatggt cacctcacat ccagagtaat taataagtgc    9600
ctccgacaaa tatttgtgca aacaaagaac agttagacac gctgtcagtg cgatagggca    9660
taaatcattg ttttatttaa catgtgtagc ataagtttac tacttaaacg gtaacattag    9720
ctcaatcatg tctctcagcc ttccgtccct tacaaccaac cctctcctgg gcacatacaa    9780
aatctaccca aatttctctt ggatatggat gaatttaatc taacctttaa ttaaaaattc    9840
tggtaaataa tttggtcatc atgtggaggc atggatgcta gttgacatta tggattttt    9900 ttatgctttc agaatcagtt tgcgttaata tagtcataag aatcacaaat tgatctttgc    9960
ctctagggaa acaagataag gatgtcattt gagagaatag ttacaggaaa ctgtatcatt   10020
ttcatgtagg ggggtgggct gtagtgaaac aaaatgataa actctgacag ttcatgcttt   10080
attctcgcat acataccttt aacgcttcga ggaagaggct gattgcatct cttaaatgtg   10140
ttccaggctt gtgttttaca tgagagagga actctactgg agctggtaga tccagactta   10200
ggatccaatt actcaacgga agaggcactc ctgatgctga acgtggctct cttatgcacc   10260
aacgcagcac cgactcttag accaaagatg tccaacgctg tgagccttct tgaaggccat   10320 accccctgc aacccttcct atcagaactc agccttgctg caaacagcct gagctcaagt    10380
ggtctacgca gaaacttctg ggaaaatcca agtgagagcc agagcataac ggcacaagca   10440
tcatataaca acaccagtga ctcgtcatct ttagatgtag atggtagctt gagacattct   10500
gcgacttaaa tgttagatgt atttcagatc tgtacacctg taagaataac tagggctatg   10560
ccactatgtc tattctggca gtacaatgta gctactaaca taaaaacacc taattctact   10620
aagaat                                                              10626

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
ctttcgtgct tatgtgggtg tgac                                          24

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
catgaggagt ctgcaataag ga                                            22

<210> SEQ ID NO 6
<211> LENGTH: 20
<212> TYPE: DNA
<213> ORGANISM: Artificial
<220> FEATURE:
<223> OTHER INFORMATION: oligonucleotide

<400> SEQUENCE: 6
ggatttgtca cgtccaacct                                               20

<210> SEQ ID NO 7
<211> LENGTH: 20
<212> TYPE: DNA
<213> ORGANISM: Artificial
<220> FEATURE:
```

```
<223> OTHER INFORMATION: oligonucleotide

<400> SEQUENCE: 7
attggcaatt gtgatagccc                                               20

<210> SEQ ID NO 8
<211> LENGTH: 24
<212> TYPE: DNA
<213> ORGANISM: Artificial
<220> FEATURE:
<223> OTHER INFORMATION: primer NBS-LRR F1

<400> SEQUENCE: 8
gctgaaccaa cccggggaga aata                                          24

<210> SEQ ID NO 9
<211> LENGTH: 24
<212> TYPE: DNA
<213> ORGANISM: Artificial
<220> FEATURE:
<223> OTHER INFORMATION: primer NBS-LRR F1

<400> SEQUENCE: 9
agatgatcgg aagaacagtg caac                                          24

<210> SEQ ID NO 10
<211> LENGTH: 10
<212> TYPE: DNA
<213> ORGANISM: Hordeum vulgare
<220> FEATURE:
<221> NAME/KEY: promoter
<222> LOCATION: (1)..(10)
<223> OTHER INFORMATION: promoter sequence motif of beta-1,3-glucanase

<400> SEQUENCE: 10
tcatcttctt                                                          10
```

METHOD FOR INCREASING RESISTANCE TO PATHOGENS IN TRANSGENIC PLANTS

RELATED APPLICATIONS

This application is a national stage application (under 35 U.S.C. §371) of PCT/EP2007/058735, filed Aug. 22, 2007, which claims benefit of European application 06119815.6, filed Aug. 30, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13477_00015_US. The size of the text file is 28 KB, and the text file was created on Feb. 24, 2009.

The present invention relates to a method of increasing the pathogen resistance in transgenic plants and/or plant cells, where a DNA sequence which codes for a protein with a leucine-rich-repeat (LRR) domain and/or a kinase activity is introduced into the plant or plant cell and expressed therein. The present invention also relates to the use of nucleic acids which code for such a protein, for the generation of transgenic plants or plant cells with an increased pathogen resistance. The present invention furthermore relates to nucleic acid sequences which code for a protein which confers an increased pathogen resistance in plants.

Plant diseases which are caused by a variety of pathogens such as, for example, viruses, bacteria and fungi can lead to considerable yield losses in crop plant cultivation, which firstly has economic consequences, but also poses a risk to human nutrition. Chemical fungicides have been employed since last century for controlling fungal diseases. While the use of these substances has made it possible to reduce the extent of plant diseases, it cannot be ruled out even now that these compounds have a harmful effect on humans, animals and the environment. In order to reduce the use of traditional plant protection products to a minimum in the long term, it is therefore important to study the natural pathogen defense of a variety of plants against different pathogens, and to exploit them, in a targeted manner, by recombinant manipulation, for example by the introduction of external resistance genes or by the manipulation of the endogenous gene expression in plants, in order to generate pathogen-resistant plants.

Only a few approaches exist which impart a resistance to pathogens, especially fungal pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defense mechanisms developed by the plant phyla, families and species interact with one another in many different ways.

Fungal pathogens have developed essentially two infection strategies. Some fungi enter into the host tissue via the stomata (for example rusts, *Septoria* species, *Fusarium* species) and penetrate the mesophyll tissue, while others penetrate via the cuticles into the epidermal cells underneath (for example *Blumeria* species).

The infections caused by the fungal pathogens lead to the activation of the plant's defense mechanisms in the infected plants. Thus, it has been possible to demonstrate that defense reactions against epidermis-penetrating fungi frequently start with the formation of a penetration resistance (formation of papillae, strengthening of the cell wall with callose as the main constituent) underneath the fungal penetration hypha (Elliott et al. Mol Plant Microbe Interact. 15: 1069-77; 2002).

In many cases, however, the plant's defense mechanisms only confer an insufficient protection mechanism against the attack by pathogens.

The formation of a penetration resistance to pathogens whose infection mechanism comprises a penetration of the epidermal cells or of the mesophyll cells is of great importance both for monocotyledonous and for dicotyledonous plants. In contrast to other approaches concerning the mediation of resistance, it can probably make possible the development of a broad-spectrum resistance to obligate biotrophic, hemibiotrophic and necrotrophic fungi.

To date, quantitative resistance traits (resistance-QTLs) have frequently been introduced by hybridization in order to generate plants with resistance to fungi. However, the disadvantage of this method is that undesirable traits are frequently also introduced. Moreover, the breeding methods required for this purpose are very complicated and time-consuming.

Accordingly, it was an object of the present invention to provide a method of increasing the resistance of plants to penetrating pathogens.

The object is achieved by the embodiments characterized in the claims.

As a consequence, the present invention relates to a method of increasing the pathogen resistance in transgenic plants and/or plant cells, where a DNA sequence which codes for a protein which mediates an increased pathogen resistance, preferably an increased resistance to fungal pathogens, is introduced into the plant or plant cell and expressed therein.

In the context of a TIGS (=Transient Induced Gene Silencing) analysis in barley using the method of Schweizer et al. (2001), it has been found that, as the result of dsRNAi-mediated silencing of the RNR8 gene, the sensitivity of the plant to the fungal pathogen *Blumeria graminis* is increased, and that the RNR8 gene might therefore play a role in conferring the pathogen resistance of barley plants.

RNR8 belongs to the family of the leucine-rich-repeat (LRR)-comprising proteins with a kinase domain or a kinase activity. Members of this family play an important role in a variety of cellular processes such as the regulation of endosperm and pollen development (Li and Wurtzel (1998) Plant Mol. Biol. 37: 749-761; Muschietti et al. (1998) Plant Cell 10: 319-330), the regulation of meristem and floral development (Torii et al. (1996) Plant Cell 8: 735-746; Clark et al. (1997) Cell 89: 575-585; Kim et al. (2000) Plant Sci. 152: 17-26) and the gibberellin-induced fruit growth (van der Knapp et al. (1999) Plant Physiol. 120: 559-569). The LRR domain comprises 2 to 45 repeats of an amino acid sequence with 20 to 30 amino acids and generally folds into the shape of a horseshoe.

It has been demonstrated by a further member of this family, OsXa21 from rice, that it confers resistance to the bacterial pathogen *Xanthomonas oryzae* (Song et al. (1995) Science 270(5243): 1804-1806). With approximately 23%, the protein according to the invention only exhibits very weak sequence homology to OsXa21.

The proteins according to the invention confer an increase of the pathogen resistance, preferably of the resistance to fungal pathogens, in plants. They are preferably distinguished by the fact that they exhibit either a leucine-rich-repeat (LRR) domain or a kinase activity; especially preferably, the proteins according to the invention exhibit both traits. Without wishing to be bound to one theory, it is currently assumed that either the kinase activity or the LRR domain or both traits together are responsible for conferring the pathogen resistance. In what follows, the term "protein according to the invention" will be used for the sake of simplicity.

The nucleic acid sequence which, in the method of the present invention, is introduced into the plant or plant cell and codes for a protein according to the invention is selected from the group consisting of:
i) nucleic acid sequences comprising nucleotide sequences which correspond to the coding sequences of SEQ ID No. 1 or fragments thereof,
ii) nucleic acid sequences comprising nucleotide sequences which code for a protein with the amino acid sequence shown in SEQ ID No. 2 or fragments of the former,
iii) nucleic acid sequences comprising nucleotide sequences which have at least 60% sequence identity with the coding sequences of SEQ ID No. 1, and/or
iv) nucleic acid sequences comprising nucleotide sequences which, under stringent conditions, hybridize with a complementary strand of a nucleotide sequence of i) to iii).

"Resistance" means the prevention, the repression, the reduction or the weakening of disease symptoms of a plant which occur as the result of infection with a pathogen. The symptoms can be different in nature, but preferably comprise those which directly or indirectly lead to an adverse effect on the quality of the plant, the quantity of the yield, the suitability for use as feedingstuff or foodstuff, or else make sowing, growing, harvesting or processing of the harvested material more difficult.

In a preferred embodiment, the following disease symptoms are weakened, reduced or prevented: development of pustules and spore beds on the surfaces of the infected tissue, maceration of the tissue, spreading necroses of the tissue, accumulation of mycotoxins, for example from *Fusarium graminearum* or *F. culmorum*.

An "increased pathogen resistance" means that the defense mechanisms of a certain plant or in a part of a plant, for example in an organ, a tissue, a cell or an organelle, show, as a result of the application of the method according to the invention, increased resistance to one or more pathogens in comparison with a suitable control, for example the wild type of the plant ("control plant", "original plant"), to which the method according to the invention has not been applied, under otherwise identical conditions (such as, for example, climatic conditions, culture conditions, pathogen species and the like). It is preferred that, in a plant, at least the epidermis and/or the mesophyll tissue or the organs which have an epidermis and/or a mesophyll tissue, show an increased resistance to the pathogens. For example, the resistance in the leaves is increased.

In one embodiment, the resistance in the lemma, the palea and/or the glum (anther primordium).

The increased resistance manifests itself preferably in a reduced manifestation of the disease symptoms, where the disease symptoms—besides the abovementioned adverse effects—also comprise for example the penetration efficiency of a pathogen into the plant or plant cell or the proliferation efficiency of the pathogen in or on the same. In this context, the disease symptoms are reduced by preferably at least 10% or at least 20%, especially preferably by at least 40% or 60%, particularly preferably by at least 70% or 80%, most preferably by at least 90% or 95%, in comparison with the control plant.

For the purposes of the invention, "pathogen" means organisms whose interactions with a plant lead to the above-described disease symptoms; in particular, pathogens mean organisms from the kingdom Fungi. The pathogen is preferably a pathogen which penetrates the epidermis or the mesophyll cells, in particular, they are pathogens which enter plants via stomata and subsequently penetrate mesophyll cells. In this context, organisms which may be mentioned by preference are those of the Ascomycota and Basidiomycota phyla. Especially preferred in this context are the families Blumeriaceae, Pucciniaceae, Mycosphaerellaceae and Hypocreaceae.

Especially preferred organisms of these families are those which belong to the genera *Blumeria*, *Puccinia*, *Fusarium* or *Mycosphaerella*.

Very especially preferred are the species *Blumeria graminis*, *Puccinia triticina*, *Puccinia striiformis*, *Mycosphaerella grarninicola*, *Stagonospora nodorum*, *Fusarium graminearum*, *Fusarium culmorum*, *Fusarium avenaceum*, *Fusarium poae* and *Microdochium nivale*.

In especially preferred embodiments, the method according to the invention leads to a resistance in
barley against the pathogen *Puccinia graminis* f.sp. hordei (barley stem rust),
in wheat against the pathogens *Fusarium graminearum*, *Fusarium avenaceum*, *Fusarium culmorum*, *Puccinia graminis* f.sp. *tritici* (wheat stem rust), *Puccinia recondita* f.sp. *tritici*, *Puccinia striiformis*, *Septoria nodorum*, *Septoria tritici* and/or *Septoria avenae*,
in maize against the pathogens *Fusarium moniliforme* var. *subglutinans*, *Puccinia sorghi* and/or *Puccinia polysora*,
in sorghum against the pathogens *Puccinia purpurea*, *Fusarium moniliforme*, *Fusarium graminearum* and/or *Fusarium oxysporum*,
in soybeans against the pathogens *Phakopsora pachyrhizi* and/or *Phakopsora meibromae*.

Another subject matter of the invention is an isolated nucleic acid molecule, comprising a nucleic acid sequence selected from the group consisting of:
i) nucleic acid sequences comprising nucleotide sequences which correspond to the coding sequences of SEQ ID No. 1 or fragments thereof,
ii) nucleic acid sequences comprising nucleotide sequences which code for a protein with the amino acid sequence shown in SEQ ID No. 2 or fragments of the former,
iii) nucleic acid sequences comprising nucleotide sequences which have at least 60% sequence identity with the coding sequences of SEQ ID No. 1, and/or
iv) nucleic acid sequences comprising nucleotide sequences which, under stringent conditions, hybridize with a complementary strand of a nucleotide sequence of i) to iii),
which codes for a protein which confers an increased pathogen resistance, preferably an increased resistance to fungal pathogens, in plants.

In a preferred embodiment, the term "nucleic acid (molecule)" as used in the present context additionally comprises the untranslated sequence located at the 3'- and at the 5-terminus of the coding gene region: at least 500, preferably 200, especially preferably 100 nucleotides of the sequence upstream of the 5'-terminus of the coding region and at least 100, preferably 50, especially preferably 20 nucleotides of the sequence downstream of the 3'-terminus of the coding gene region.

An "isolated" nucleic acid molecule is separated from other nucleic acid molecules which are present in the natural source of the nucleic acid. An "isolated" nucleic acid preferably does not have any sequences which naturally flank the nucleic acid in the genomic DNA of the organism from which the nucleic acid originates (for example sequences located at the 5'- and 3'-termini of the nucleic acid). In various embodiments, the isolated molecule may comprise for example fewer than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid originates. All the nucleic acid molecules mentioned here may take the form of, for example, RNA, DNA or cDNA.

The nucleic acid molecules used in the method, for example a nucleic acid molecule with a nucleotide sequence of SEQ ID No. 1 or a part thereof, can be isolated using standard techniques of molecular biology and the sequence information provided herein. Also, it is possible to identify for example an homologous sequence, or homologous, conserved sequence regions, at the DNA or amino acid level using comparative algorithms as can be found for example on the NCBI homepage at http://www.ncbi.nlm.nih.gov. Essential parts of this sequence, or the entire homologous sequence, can be used as hybridization probe using standard hybridization techniques (such as, for example, described in Sambrook et al., vide supra) for isolating, from other organisms, further nucleic acid sequences which are useful in the method, by screening cDNA libraries and/or genomic libraries. Moreover, a nucleic acid molecule comprising a complete sequence as shown in SEQ ID No. 1 or a part thereof can be isolated by a polymerase chain reaction, where oligonucleotide primers based on the sequences stated herein or of parts thereof are used (for example, a nucleic acid molecule comprising the complete sequence or a part thereof can be isolated by a polymerase chain reaction using oligonucleotide primers which have been generated on the basis of the same sequence). For example mRNA can be isolated from cells (for example by the guanidinium thiocyanate extraction method by Chirgwin et al. (1979) Biochemistry 18; 5294-5299), and cDNA can be generated therefrom by means of reverse transcriptase (for example Moloney MLV reverse transcriptase, obtainable from Gibco/BRL, Bethesda, Md. or AMV reverse transcriptase, obtainable from Seikagaku Amerika, Inc., St. Petersburg, Fla.). Synthetic oligonucleotide primers for amplification by means of a polymerase chain reaction can be generated on the basis of the nucleic acid sequence shown in SEQ ID No. 1 or with the aid of the amino acid sequence shown in SEQ ID No. 2. A nucleic acid according to the invention can be amplified by means of standard PCR amplification techniques using cDNA or alternatively using genomic DNA as the template and suitable oligonucleotide primers. The nucleic acid thus amplified can be cloned into a suitable vector and characterized by means of DNA sequence analysis. Oligonucleotides which correspond to a nucleotide sequence which codes for a protein according to the invention can be generated by standard synthetic methods, for example using an automatic DNA synthesizer.

The term "sequence identity" between two nucleic acid sequences is understood as meaning the identity of the nucleic acid sequence over the entire sequence length in each case, in a preferred embodiment over the entire expressed sequence length, preferably cDNA, even more preferably over the coding sequence, preferably CDS, which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25: 3389ff), with the following parameters being set:

| Gap Weight: 50 | Length Weight: 3 |
|---|---|
| Average Match: 10 | Average Mismatch: 0 |

For example, a sequence with at least 80% homology at the nucleic acid level with the sequence SEQ ID No. 1 will, upon comparison with the sequence of SEQ ID No. 1 using the above program algorithm with the above parameter set, have at least 80% homology.

In one embodiment, the present invention relates to nucleic acid sequences which have at least 60%, preferably at least 65, 70, 75 or 80%, especially preferably at least 82, 84, 86, 88 or 90% and most preferably at least 92, 94, 96, 98 or 99% sequence identity to the sequence shown in SEQ ID No. 1.

"Identity between two proteins" is understood as meaning the identity of the amino acids over a specific protein region, preferably over the entire protein length, in particular the identity which is calculated by comparison with the aid of software, for example the Lasergene Software from DNA Star Inc., Madison, Wis. (USA) using the CLUSTAL method (Higgins et al. (1989) Comput. Appl. Biosci. 5(2): 151). Homologies can also be calculated with the aid of the Lasergene software from DNA Star Inc., Madison, Wis. (USA) using the CLUSTAL method (Higgins et al. (1989) Comput. Appl. Biosci. 5(2): 151).

Preferably, "identity between two proteins" is understood as meaning the identity of the amino acid sequence over the entire sequence length in each case, which is calculated by comparison with the aid of the program algorithm GAP (Wisconsin Package Version 10.0, University of Wisconsin, Genetics Computer Group (GCG), Madison, USA) the following parameters being set:

| Gap Weight: 8 | Length Weight: 2 |
|---|---|
| Average Match: 2 912 | Average Mismatch: 2 003 |

"Standard hybridization conditions" is to be understood in a broad sense and means, depending on the application, stringent or less stringent hybridization conditions. Such hybridization conditions are described, inter alia, in Sambrook and Russell, Molecular Cloning—A Laboratory Manual, 3rd edition, Cold Spring Harbor Laboratory Press, 2001) or in Current Protocols in Molecular Biology, John Wiley & Sons, N.Y. (1989), 6.3.1-6.3.6.

The skilled worker would choose hybridization conditions which allow him to distinguish between specific and unspecific hybridizations.

For example, the conditions during the wash step can be selected from among low-stringency conditions (with approximately 2×SSC at 50° C.) and high-stringency conditions (with approximately 0.2×SSC at 50° C., preferably at 65° C.) (20×SSC: 0.3M sodium citrate, 3M NaCl, pH 7.0). In addition, the temperature may be raised during the wash step from low-stringency conditions at room temperature, i.e. approximately 22° C., up to higher-stringency conditions at approximately 65° C. Both parameters, salt concentration and temperature can be varied simultaneously or else individually, the other parameter in each case being kept constant. It is also possible to employ denaturing agents such as, for example, formamide or SDS during the hybridization. In the presence of 50% formamide, the hybridization is preferably carried out at 42° C. Some examples of conditions for hybridization and wash step are given hereinbelow:

(1) Hybridization conditions may be selected for example from among the following conditions:
   a) 4×SSC at 65° C.,
   b) 6×SSC at 45° C.,
   c) 6×SSC, 100 μg/ml denatured fragmented fish sperm DNA at 68° C.,
   d) 6×SSC, 0.5% SDS, 100 μg/ml denatured, fragmented salmon sperm DNA at 68° C.,
   e) 6×SSC, 0.5% SDS, 100 μg/ml denatured, fragmented salmon sperm DNA, 50% formamide at 42° C.,
   f) 50% formamide, 4×SSC at 42° C.,
   g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
   h) 2× or 4×SSC at 50° C. (low-stringency condition),
   i) 30 to 40% formamide, 2× or 4×SSC at 42° C. (low-stringency condition),
   j) 500 mM sodium phosphate buffer pH 7.2, 7% SDS (g/V), 1 mM EDTA, 10 μg/ml single stranded DNA, 0.5% BSA (g/V) (Church and Gilbert (1984) Proc. Natl. Acad. Sci. U.S.A. 81(7): 1991-1995.)
(2) Wash steps can be selected for example from among the following conditions:
   a) 0.015M NaCl/0.0015 M sodium citrate/0.1% SDS at 50° C.,
   b) 0.1×SSC at 65° C.,
   c) 0.1×SSC, 0.5% SDS at 68° C.,
   d) 0.1×SSC, 0.5% SDS, 50% formamide at 42° C.,
   e) 0.2×SSC, 0.1% SDS at 42° C.,
   f) 2×SSC at 65° C. (low-stringency condition).

In one embodiment, the hybridization conditions are selected as follows:

A hybridization buffer comprising formamide, NaCl and PEG 6000 is chosen. The presence of formamide in the hybridization buffer destabilizes double-stranded nucleic acid molecules, which makes it possible to lower the hybridization temperature to 42° C. without thereby reducing stringency. The use of salt in the hybridization buffer increases the renaturation rate of a Duplex, or the hybridization efficiency. Although PEG increases the viscosity of the solution, which has an adverse effect on renaturation rates, the presence of the polymer in the solution increases the concentration of the probe in the remaining medium, which enhances the hybridization rate. The composition of the buffer is as follows:

| Hybridization buffer |
| --- |
| 250 mM sodium phosphate buffer pH 7.2 |
| 1 mM EDTA |
| 7% SDS (g/v) |
| 250 mM NaCl |
| 10 μg/ml ssDNA |
| 5% Polyethylene glycol (PEG) 6000 |
| 40% Formamide |

The hybridizations are carried out overnight at 42° C. The following morning, the filters are washed 3× with 2×SSC+ 0.1% SDS for approximately 10 min in each case.

Nucleic acid sequences which deviate from the nucleic acid sequence shown in SEQ ID No. 1 can be generated for example by introducing one or more nucleotide substitutions, additions or deletions into a nucleotide sequence of SEQ ID No. 1 so that proteins are generated into which one or more amino acid substitutions, additions or deletions have been introduced in comparison with the sequence shown in SEQ ID No. 2. Mutations can be introduced into the sequence of SEQ ID No. 1 by means of standard techniques, such as, for example, site-specific mutagenesis and PCR-mediated mutagenesis. It is preferred to generate conservative amino acid substitutions on one or more of the predicted nonessential amino acid residues, that is to say on amino acid residues which have no effect on the kinase activity and/or on the LRR domain. In a "conservative amino acid substitution", an amino acid residue is exchanged for an amino acid residue with a similar side chain. Families of amino acid residues with similar side chains have been defined in the art. These families comprise amino acids with basic side chains (for example lysine, arginine, histidine), acidic side chains (for example aspartic acid and glutamic acid), uncharged polar side chains (for example glycine, asparagine, glutamine, serine, threonine, tyrosine, cysteine), unpolar side chains (for example alanine, valine, leucine, isoleucine, proline, phenylalanine, methionine, tryptophan), beta-branched side chains (for example threonine, valine, isoleucine) and aromatic side chains (for example tyrosine, phenylalanine, tryptophan). A predicted nonessential amino acid residue in the protein used in accordance with the invention is thus preferably exchanged for another amino acid residue from the same side-chain family. As an alternative, it is possible, in another embodiment, to introduce the mutations randomly over the entire sequence, or part of the sequence, which codes for the protein according to the invention, for example to screen for their ability of conferring pathogen resistance.

The term "DNA fragments" as used in the present context is understood as meaning DNA portions which code for a protein according to the invention, whose biological activity consists in that it confers an increase of the pathogen resistance. The DNA fragments preferably code for a protein with a kinase activity or with an LRR domain, especially preferably with both traits, where the proteins encoded by the DNA portions have essentially the same kinase activity and/or the same LRR domain as the proteins encoded by the complete DNA sequence and where the increase according to the invention of the pathogen resistance can be achieved in transgenic plants using these fragments.

The term "protein fragments" as used in the present context is understood as meaning protein portions whose biological activity consists in that it confers an increase of the pathogen resistance (preferably the resistance of fungal pathogens) in plants. The protein fragments preferably have a kinase activity or an LRR domain, especially preferably both traits, where the protein portions have essentially the same kinase activity and/or the same LRR domain as the full-length protein and where the increase according to the invention of the pathogen resistance can be achieved in transgenic plants using these fragments.

The term "essentially identical enzymatic activity" of the protein with kinase activity used in the method according to the invention means that the enzymatic activity in comparison with the enzymes encoded by the sequence with SEQ ID No. 1 or its derivatives is still at least 50%, preferably at least 60%, especially preferably at least 70%, particularly preferably at least 80% and most preferably at least 90%. Thus, proteins with kinase activity with an essentially identical enzymatic activity are also suitable for bringing about an increased pathogen resistance in transgenic plants.

The kinase activity of proteins can be determined by simple methods which are known to the skilled worker and which are referred to as kinase assays. To this end, for example, the protein which is to be tested, and which has been purified by, for example, immunoprecipitation, is incubated in a suitable buffer with radiolabeled ATP as the phosphate donor and with a suitable substrate, and the substrate is subsequently separated via an SDS-polyacrylamide gel. If the protein has a kinase activity, the substrate is labeled with the radiolabeled phosphate, and the radioactivity can be detected and quantitatively determined using suitable methods.

The increase according to the invention of the pathogen resistance can also be achieved by manipulating the expression of the plant-intrinsic endogenous protein, which corresponds to the protein according to the invention. This is, thus, a plant-intrinsic protein which confers an increase of the pathogen resistance which preferably has a kinase activity or an LRR domain, and especially preferably both traits. This manipulation of the protein expression can be achieved for example by modifying the promoter DNA sequence of the protein-encoding gene. Such a modification, which results in a modified, preferably increased, expression rate of the endogenous gene according to the invention, can be effected by deleting or inserting DNA sequences. A modification of the promoter sequence of endogenous genes according to the invention will, as a rule, lead to a modification of the expressed amount of the gene and thus, for example, also to a modification of the kinase activity which can be detected in the cell, or in the plants (if the protein has kinase activity). The modification of the promoter sequence of the endogenous gene according to the invention can also lead to a modification of the amount of protein with an LRR domain in the cell.

Another possibility for increasing the activity and the content of the endogenous protein according to the invention is to regulate transcription factors which are involved in the transcription of the respective endogenous gene according to the invention, for example by overexpression. The measures for overexpressing transcription factors are known to the skilled worker and are also disclosed for proteins according to the invention within the scope of the present invention.

Furthermore, an increased expression of an endogenous gene according to the invention can be achieved by a regulator protein which does not occur in the untransformed organism interacting with the promoter of these genes. Such a regulator can take the form of a chimeric protein which consists of a DNA binding domain and a transcription activator domain, as described, for example, in WO 96/06166.

Regarding a nucleic acid sequence, an expression cassette or a vector comprising said nucleic acid sequence or an organism transformed with said nucleic acid sequence, expression cassette or vector, "transgenic" means, for example, all those constructs or organisms which exist as a result of recombinant methods and in which either
a) the RNR8 nucleic acid sequence, or
b) a genetic control sequence, for example a promoter, which is operably linked with the RNR8 nucleic acid sequence, or
c) (a) and (b)
are not in their natural genetic environment or have been modified by recombinant methods, it being possible for the modification to be, for example, a substitution, addition, deletion, or insertion of one or more nucleotide residues. "Natural genetic environment" means the natural chromosomal locus in the organism of origin or the presence in a genomic library. In the case of a genomic library, the natural genetic environment of the nucleic acid sequence is preferably retained at least in part. The environment flanks the nucleic acid sequence at least on one side and has a sequence length of at least 50 bp, preferably at least 500 bp, especially preferably at least 1000 bp, very especially preferably at least 5000 bp. A naturally occurring expression cassette—for example the naturally occurring combination of the RNR8 promoter with the corresponding RNR8 gene—becomes a transgenic expression cassette when it is modified by non-natural, synthetic ("artificial") methods such as, for example, mutagenization. Such methods are described (U.S. Pat. No. 5,565,350; WO 00/15815).

Within the scope of the present invention, "introduction" means all methods which are suitable for introducing an RNR8 nucleic acid sequence directly or indirectly into a plant or a cell, compartment, tissue, organ or seed thereof, or for generating it therein. The introduction can lead to a transient or to a stable presence of an RNR8 nucleic acid sequence.

For example, "introduction" comprises methods such as transfection, transduction or transformation.

The introduction, into an organism or cells, tissues, organs, parts or seeds of the same (preferably into plants or plant cells, tissues, organs, parts or seeds), of an expression cassette according to the invention can advantageously be carried out using vectors in which the expression cassettes are present. The expression cassette can be introduced into the vector (for example a plasmid) via a suitable restriction cleavage site. The resulting plasmid is first introduced into E. coli cells. Correctly transformed E. coli cells are selected, cultured, and the recombinant plasmid is obtained by methods known to the skilled worker. The cloning step may be verified by restriction analysis and sequencing.

The vectors may take the form of, for example, plasmids, cosmids, phages, viruses or else agrobacteria. In an advantageous embodiment, the expression cassette is introduced by means of plasmid vectors. Preferred vectors are those which make possible a stable integration of the expression cassette into the host gene.

The generation of a transformed organism (or of a transformed cell) requires that the relevant DNA molecule is introduced into the relevant host cell and that the corresponding RNAs and proteins are subsequently formed by gene expression.

A multiplicity of methods (Keown et al. (1990) Methods in Enzymology 185: 527-537) are available for this procedure, which is referred to as transformation (or transduction or transfection). Thus, for example, the DNA or RNA can be introduced directly by microinjection or else by bombardment with DNA-coated microparticles. Also, the cell can be permeabilized chemically, for example using polyethylene glycol, with the result that said DNA may enter the cell ends by diffusion. The DNA may also be introduced into the cell by means of protoplast fusion with other DNA-comprising units such as minicells, cells, lysosomes or liposomes. A further suitable method of introducing DNA is electroporation, where the cells are permeabilized reversibly by an electrical pulse. Suitable methods have been described (for example in Bilang et al. (1991) Gene 100: 247-250; Scheid et al. (1991) Mol. Gen. Genet. 228: 104-112; Guerche et al. (1987) Plant Science 52: 111-116; Neuhause et al. (1987) Theor. Appl. Genet. 75: 30-36; Klein et al. (1987) Nature 327: 70-73; Howell et al. (1980) Science 208: 1265; Horsch et al. (1985) Science 227: 1229-1231; DeBlock et al. (1989) Plant Physiology 91: 694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the methods described are exploited for the transformation and regeneration of plants from plant tissue or plant cells for the purpose of transient or stable transformation. Suitable methods are mainly protoplast transformation by means of polyethylene-glycol-induced DNA uptake, the biolistic method with the gene gun, the method known as the particle bombardment method, electroporation, the incubation of dry embryos in DNA-comprising solution, and microinjection.

Besides these "direct" transformation techniques, a transformation may also be carried out by bacterial infection by means of *Agrobacterium tumefaciens* or *Agrobacterium rhizogenes*. The methods are described for example in Horsch et al. (1985) Science 225: 1229f.

If Agrobacteria are used, the expression cassette must be integrated into specific plasmids, which may either take the form of a shuttle or intermediate vector or of a binary vector. If a Ti or Ri plasmid is used for the transformation, at least the right border, but in most cases both the right and the left borders, of the Ti or Ri plasmid T-DNA is linked in the form of a flanking region with the expression cassette to be introduced.

It is preferred to use binary vectors. Binary vectors are capable of replication both in *E. coli* and in *Agrobacterium*. As a rule, they comprise a selection marker gene and a linker or polylinker flanked by the right and left T-DNA border sequences. They can be transformed directly into *Agrobacterium* (Holsters et al. (1978) Mol. Gen. Genet. 163: 181-187). The selection marker gene, for example the nptII gene, which confers resistance to Kanamycin, permits a selection of transformed Agrobacteria. The *Agrobacterium* which acts as the host organism in this case should already comprise a Helfer Ti-plasmid with the vir region, which is required for the transfer of the T-DNA into the plant cell. An *Agrobacterium* thus transformed can be used for transforming plant cells. The use of T-DNA for the transformation of plant cells has been researched intensively and is described in (EP 120 516; Hoekema, In: The Binary Plant Vector System, Offsetdrukkerij Kanters B. V., Alblasserdam, Chapter V; An et al. (1985) EMBO J 4: 277-287). A variety of binary vectors are known, some of which are commercially available, such as, for example, pBI101.2 or pBIN19 (Clontech Laboratories, Inc. USA).

In the case of injection or electroporation of DNA or RNA into plant cells, the plasmid used does not need to meet any particular requirements. It is possible to use simple plasmids, such as those from the pUC series. If intact plants are to be regenerated from the transformed cells, it is required that an additional selectable marker gene is located in the plasmid.

Stably transformed cells, i.e. those which comprise the introduced DNA integrated into the DNA of the host cell, can be distinguished from untransformed cells when a selectable marker is part of the introduced DNA (McCormick et al. (1986) Plant Cell Reports 5: 81-84). For example, any gene which is capable of conferring resistance to antibiotics or herbicides (such as kanamycin, G 418, bleomycin, hygromycin or phosphinothricin), may be used as a marker. Transformed cells which express such a marker gene are capable of surviving the presence of concentrations of a relevant antibiotic or herbicide which kill an untransformed wild type. Examples comprise the bar gene, which confers resistance to the herbicide phosphinothricin (Rathore et al. (1993) Plant Mol Biol 21(5): 871-884), the nptII gene, which confers resistance to kanamycin, the hpt gene, which confers resistance to hygromycin, or the EPSP gene, which confers resistance to the herbicide glyphosate. The resulting plants can be bred and hybridized in the customary manner. Two or more generations should be grown in order to ensure that the genomic integration is stable and hereditary.

The abovementioned methods are described, for example, in Jenes et al. (1993) Techniques for Gene Transfer, in: Transgenic Plants, Vol. 1, Engineering and Utilization, edited by SD Kung and R Wu, Academic Press, p. 128-143 and in Potrykus (1991) Annu. Rev. Plant Physiol. Plant Molec. Biol. 42: 205-225). It is preferred to clone the construct to be expressed into a vector which is suitable for transforming *Agrobacterium tumefaciens*, for example into pBin19 (Bevan et al. (1984) Nucl. Acids Res. 12: 8711f).

As soon as a transformed plant cell has been generated, an intact plant can be obtained using methods known to the skilled worker. The starting material here is, for example, callus cultures. It is possible to induce, from these as yet undifferentiated cell biomasses, the formation of shoot and root in the known manner. The plantlets obtained can be planted out and used for cultivation.

The person skilled in the art also knows methods for regenerating plant parts and intact plants from plant cells. Methods for this purpose are described, for example, by Fennell et al. (1992) Plant Cell Rep. 11: 567-570; Stoeger et al (1995) Plant Cell Rep. 14: 273-278; Jahne et al. (1994) Theor. Appl. Genet. 89: 525-533.

A further subject of the present invention is a recombinant nucleic acid molecule comprising the following elements in 5'-3' orientation:
  regulatory sequences of a promoter which is active in plant cells,
  a DNA sequence according to the invention in operable linkage thereto,
  if appropriate, regulatory sequences which may act as transcription, termination and/or polyadenylation signals in the plant cell, in operable linkage thereto.

"In operable linkage" means that a promoter and the nucleic acid sequence to be expressed and, if appropriate, further regulatory elements are arranged in such a way that each of the regulatory elements can fulfill its function when the nucleic acid sequence is expressed. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as the promoter, so that the two sequences are linked covalently to each other. The distance between the promoter sequence and the nucleic acid sequence to be expressed recombinantly is preferably less than 200 base pairs, especially preferably less than 100 base pairs and most preferably less than 50 base pairs.

Operable linkage, and a recombinant nucleic acid molecule, can be generated by means of customary recombination and cloning techniques as are described, for example, in Sambrook and Russell (2001) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or as a signal peptide, may also be positioned between the promoter nucleic acid molecule to be expressed. The insertion of sequences may also lead to the expression of fusion proteins. Preferably, the recombinant nucleic acid molecule, comprising an operable linkage of at least a promoter and the nucleic acid sequence to be expressed, can exist in a vector-integrated form and be inserted into a plant genome, for example by transformation.

The term plant-specific promoters is understood as meaning, in principle, any promoter which is capable of governing the expression of genes, in particular foreign genes, in plants or plant parts, plant cells, plant tissues, or plant cultures. Here, expression may be for example, constitutive, inducible or development-dependent.

The following are preferred:

a) Constitutive Promoters

"Constitutive" promoter is understood as meaning those promoters which ensure expression in a large number of, preferably all, tissues over a substantial period of plant development, preferably at all stages of plant development. In particular a plant promoter or a promoter derived from a plant virus are preferably used. Particularly preferred is the promoter of the CaMV cauliflower mosaic virus 35S transcript (Franck et al. (1980) Cell 21: 285-294; Odell et al. (1985) Nature 313: 810-812; Shewmaker et al. (1985) Virology 140: 281-288; Gardner et al. (1986) Plant Mol Biol 6: 221-228) or the 19S CaMV promoter (U.S. Pat. No. 5,352,605; WO 84/02913; Benfey et al. (1989) EMBO J. 8: 2195-2202). Another suitable constitutive promoter is the "Rubisco small subunit (SSU)" promoter (U.S. Pat. No. 4,962,028), the *Agrobacterium* nopaline synthase promoter, the TR dual promoter, the *Agrobacterium* OCS (octopine synthase) promoter, the ubiquitin promoter (Holtorf S et al. (1995) Plant Mol Biol 29: 637-649), the ubiquitin 1 promoter (Christensen et al. (1992) Plant Mol Biol 18: 675-689; Bruce et al. (1989) Proc. Natl. Acad. Sci. USA 86: 9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker. Especially preferred as constitutive promoter is the promoter of the nitrilase-1 (nit1) gene from *A. thaliana* (GenBank Acc. No.: Y07648.2, Nukleotide 2456-4340, Hillebrand et al. (1996) Gene 170:197-200).

b) Tissue-Specific Promoters

In one embodiment, promoters with specificity for the anthers, ovaries, flowers, leaves, stems, roots and seeds are used.

Seed-specific promoters are such as, for example, the phaseolin promoter (U.S. Pat. No. 5,504,200; Bustos et al. (1989) Plant Cell 1(9): 839-53), the 2S albumin gene promoter (Joseffson et al. (1987) J. Biol. Chem. 262: 12196-12201), the legumin promoter (Shirsat et al. (1989) Mol. Gen. Genet. 215(2): 326-331), the USP (unknown seed protein) promoter; Bäumlein et al. (1991) Mol. Gen. Genet. 225(3): 459-67), the napin gene promoter (U.S. Pat. No. 5,608,152; Stalberg et al. (1996) L. Planta 199: 515-519), the promoter of the gene coding for sucrose binding protein (WO 00/26388) or the legumin B4 promoter (LeB4; Bäumlein et al. (1991) Mol. Gen. Genet. 225: 121-128; Bäumlein et al. (1992) Plant Journal 2(2): 233-9; Fiedler et al. (1995) Biotechnology (NY3) 13(10): 1090f), the *Arabidopsis* oleosin promoter (WO 98/45461), the *Brassica* Bce4 promoter (WO 91/13980). Further suitable seed-specific promoters are those of the genes coding for the high-molecular-weight glutenin (HMWG), gliadin, branching enzyme, ADP glucose pyrophosphatase (AGPase). Further preferred promoters are those which permit seed-specific expression in monocots such as maize, barley, wheat, rye, rice and the like. The following can be employed advantageously: the promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the zein gene, the kasirin gene, or the secalin gene).

Tuber-, storage-root- or root-specific promoters are, for example, the patatin promoter class I (B33), the potato cathepsin D inhibitor promoter.

Leaf-specific promoters are, for example, the potato cytosolic FBPase promoter (WO 97/05900), the SSU promoter (small subunit) of Rubisco (ribulose-1,5-bisphosphate carboxylase) or the ST-LSI promoter from potato (Stockhaus et al. (1989) EMBO J 8: 2445-2451). Epidermis-specific promoters are, for example, the OXLP gene (oxalate-oxidase-like protein) promoter (Wei et al. (1998) Plant Mol Biol 36: 101-112), a promoter consisting of the GSTA1 promoter and WIR1a intron (WO 2005/035766) and the GLP4 promoter (PCT/EP 2006/062747).

Other tissue-specific promoters are, for example, flower-specific promoters such as, for example, the phytoen synthase promoter (WO 92/16635) or the promoter of the Prr gene (WO 98/22593), and anther-specific promoters such as the 5126 promoter (U.S. Pat. No. 5,689,049, U.S. Pat. No. 5,689,051), the global promoter and the γ-zein promoter.

c) Chemically Inducible Promoters

The expression cassettes can also comprise a chemically inducible promoter (review article: Gatz et al. (1997) Annu. Rev. Plant Physiol. Plant Mol. Biol. 48: 89-108), by which the expression of the exogenous gene in the plant at a particular point in time can be controlled. Such promoters such as, for example, the PRP1 promoter (Ward et al. (1993) Plant Mol. Biol. 22: 361-366), a salicylic-acid-inducible promoter (WO 95/19443), a benzenesulfonamide-inducible promoter (EP 0 388 186), a tetracyclin-inducible promoter (Gatz et al. (1992) Plant J 2: 397-404), an abscisic-acid-inducible promoter (EP 0 335 528) or an ethanol- or cyclohexanone-inducible promoter (WO 93/21334) can likewise be used.

d) Stress or Pathogen-Inducible Promoters

Very especially advantageous is the use of pathogen-inducible promoters since these make possible expression only when required (i.e. infection with pathogens).

Thus, promoters which are used in one embodiment in the method according to the invention are active promoters, which are pathogen-inducible promoters.

Pathogen-inducible promoters comprise the promoters of genes which are induced as a consequence of infection by pathogens, such as, for example, genes of PR proteins, SAR proteins, β-1,3-glucanase, chitinase and the like (for example Redolfi et al. (1983) Neth. J. Plant Pathol. 89: 245-254; Uknes et al. (1992) Plant Cell 4: 645-656; Van Loon (1985) Plant Mol. Virol. 4: 111-116; Marineau et al. (1987) Plant Mol. Biol. 9: 335-342; Matton et al. (1987) Molecular Plant-Microbe Interactions 2: 325-342; Somssich et al. (1986) Proc. Natl. Acad. Sci USA 83: 2427-2430; Somssich et al. (1988) Mol. Gen. Genetics 2: 93-98; Chen et al. (1996) Plant J 10: 955-966; Zhang and Sing (1994) Proc. Natl. Acad. Sci. USA 91: 2507-2511; Warner et al. (1993) Plant J. 3: 191-201; Siebertz et al. (1989) Plant Cell 1: 961-968).

Also comprised are wound-inducible promoters such as that of the pinII gene (Ryan (1990) Ann. Rev. Phytopath 28: 425-449; Duan et al. (1996) Nat. Biotech. 14: 494-498), of the wun1 and wun2 gene (U.S. Pat. No. 5,428,148), of the win1 and win2 gene (Stanford et al. (1989) Mol. Gen. Genet. 215: 200-208), of the systemin gene (McGurl et al. (1992) Science 225: 1570-1573), of the WIP1 gene (Rohmeier et al. (1993) Plant Mol. Biol. 22: 783-792; Eckelkamp et al. (1993) FEBS Letters 323: 73-76), of the MPI gene (Corderok et al. (1994) Plant J 6(2): 141-150) and the like.

A source for further pathogen-inducible promoters is the PR gene family. A series of elements in these promoters have proven to be advantageous. Thus, the nucleotide region from nucleotide −364 to nucleotide −288 in the PR-2d promoter confers salicylate specificity (Buchel et al. (1996) Plant Mol. Biol. 30: 493-504). The sequence 5'-TCATCTTCTT-3' occurs repeatedly in the promoter of the barley β-1,3-glucanase and in more than 30 further stress-induced genes. In tobacco, this region binds a nuclear protein whose quantity is increased by salicylate. The PR-1 promoters from tobacco and *Arabidopsis* (EP-A 0 332 104, WO 98/03536) are also suitable as pathogen-inducible promoters. Preferred, since they are induced particularly specifically by pathogens, are the "acidic PR-5" (aPR5) promoters from barley (Schweizer et al. (1997) Plant Physiol. 114: 79-88) and wheat (Rebmann et al. (1991) Plant Mol. Biol. 16: 329-331). aPR5 proteins accumulate in approximately 4 to 6 hours after infection with pathogens and only show very little background expression (WO 99/66057). An approach for achieving an increased pathogen-induced specificity is the generation of synthetic promoters from combinations of known pathogen-responsive elements (Rushton et al. (2002) Plant Cell 14: 749-762; WO 00/01830; WO 99/66057). Further pathogen-inducible promoters from different species are known to the skilled worker (EP-A 1 165 794; EP-A 1 062 356; EP-A 1 041 148; EP-A 1 032 684).

Further pathogen-inducible promoters comprise the flacks Fis1 promoter (WO 96/34949), the Vst1 promoter (Schubert et al. (1997) Plant Mol. Biol. 34: 417-426) and the EAS4 sesquiterpene cyclase promoter from tobacco (U.S. Pat. No. 6,100,451).

Further preferred promoters are those which are induced by biotic or abiotic stress, such as, for example, the pathogen-inducible promoter of the PRP1 gene (or gst1 promoter), for example from potato (WO 96/28561; Ward et al. (1993) Plant Mol. Biol. 22: 361-366), the heat-inducible hsp70 or hsp80 promoter from tomato (U.S. Pat. No. 5,187,267), the chill-inducible alpha-amylase promoter from potato (WO 96/12814), the light-inducible PPDK promoter or the wound-induced pinII promoter (EP-A 0 375 091).

e) Mesophyll-Tissue-Specific Promoters

"Mesophyll tissue" means the leaf tissue between the layers of the epidermis, consisting of the palisade tissue, the spongy tissue and the leaf veins.

One embodiment of the method according to the invention employs mesophyll-tissue-specific promoters such as, for example, the promoter of the wheat germin 9f-3.8 gene (Gen-Bank Acc.-No.: M63224) or the barley GerA promoter (WO 02/057412). Said promoters are especially advantageous since they are both mesophyll-tissue-specific and pathogen-inducible. Further suitable is the mesophyll-tissue-specific *Arabidopsis* CAB-2 promoter (Genrank Acc.-No.: X15222) and the *Zea mays* PPCZm1 promoter (GenBank Acc.-No.: X63869) or homologues thereof. Mesophyll-tissue-specific means that the transcription of a gene is limited as a result of the specific interaction of Cis elements present in the promoter sequence and transcription factors binding to these elements and is limited to the smallest possible amount of plant tissue comprising mesophyll tissue; preferably, it means transcription limited to the mesophyll tissue.

Further mesophyll-specific promoters are PPCZm1 (=PEPC; Kausch (2001) Plant Mol. Biol. 45: 1-15); OsrbcS (Kyozuka et al. (1993) Plant Phys. 102: 991-1000); OsPPDK, ace. AC099041; TaGF-2.8, acc. M63223 (Schweizer (1999) Plant J. 20: 541-552; TaFBPase, acc. X53957; TaWIS1, acc. AF467542 (US 2002/115849); HvBIS1, acc. AF467539 (US 2002/115849); ZmMIS1, acc. AF467514 (US 2002/115849); HvPR1a, acc. X74939 (Bryngelsson et al. (1994) Molecular Plant-Microbe Interactions 7(2): 267-75; HvPR1b, acc. X74940 (Bryngelsson et al. (1994) Molecular Plant-Microbe Interactions 7(2): 267-75); HvB1, 3gluc; acc. AF479647; HvPrx8, acc. AJ276227 (Kristensen et al (2001) Molecular Plant Pathology 2(6); 311-317; and HvPAL, acc. X97313 (Wei (1998) Plant Molecular Biology 36: 101-112).

f) Epidermis-Specific Promoters

"Epidermis tissue" or epidermis means the outermost tissue layers of plants. The epidermis can have one or more layers; epidermis-"enriched" gene expression exists, such as, for example, that of Cer3, which may act as marker (Hannoufa. (1996) Plant J. 10 (3): 459-467).

By "epidermis", the skilled worker preferably means the prevailing epidermal tissue of primary aerial plant parts, for example of the shoot, of the leaves, flowers, fruits and seeds.

Examples of epidermis-specific promoters are WIR5 (=GstA1), acc. X56012 (Dudler & Schweizer, unpublished); GLP4, acc. AJ310534 (Wei (1998) Plant Molecular Biology 36. 101-112); GLP2a, acc. AJ237942 (Schweizer (1999). Plant J 20: 541-552); Prx7, acc. AJ003141 (Kristensen (2001) Molecular Plant Pathology 2(6); 311-317); GerA, acc. AF250933 (Wu (2000) Plant Phys. Biochem. 38: 685-698); (OsROC1, acc. AP004656; RTBV, acc. AAV62708, AAV62707 (Klöti (1999) PMB 40: 249-266) and Cer3 (Hannoufa (1996) Plant J. 10 (3): 459-467).

g) Development-Dependent Promoters

Further suitable promoters are, for example, fruit-maturation-specific promoters such as, for example, the tomato fruit-maturation-specific promoter (WO 94/21794, EP 409 625). Development-dependent promoters partly comprise the tissue-specific promoters, since individual tissues develop by nature in a development-dependent fashion.

Especially preferred are constitutive promoters, and also leaf- and/or stem-specific, pathogen-inducible, root-specific, mesophyll-tissue-specific promoters, with constitutive, pathogen-inducible, mesophyll-tissue-specific and root-specific promoters being most preferred.

Further promoters may further be operably linked with the nucleic acid sequence to be expressed, which promoters make possible expression in further plant tissues or in other organisms such as, for example, *E. coli* bacteria. Plant promoters which are suitable are, in principle, all the above-described promoters.

Further promoters which are suitable for expression in plants are described (Rogers et al. (1987) Meth. in Enzymol. 153: 253-277; Schardl et al. (987) Gene 61: 1-11; Berger et al. (1989) Proc. Natl. Acad. Sci. USA 86; 8402-8406).

Moreover, the average person skilled in the art is capable of isolating further suitable promoters by means of routine methods. Thus, the person skilled in the art can identify for example further epidermis-specific regulatory nucleic acid elements, using customary methods of molecular biology, for example hybridization experiments or DNA-protein binding studies. Here, a first step consists in, for example, isolating the desired tissue from the desired organism, from which the regulatory sequences are to be isolated, and in isolating the total poly(A)$^+$ RNA therefrom and establishing a cDNA library. In a second step, those clones from the first library are identified, by means of hybridization, whose corresponding poly(A)$^+$ RNA molecules accumulate in the desired tissue only, which identification is carried out with the aid of cDNA clones which are based on poly(A)$^+$ RNA molecules from another tissue. Thereafter, promoters which have tissue-specific regulatory elements are isolated with the aid of these cDNAs which have been thus identified. Moreover, the person skilled in the art has available further PCR-based methods for the isolation of suitable tissue-specific promoters.

The nucleic acid sequences present in the expression cassettes or vectors according to the invention may be operably linked with further genetic control sequences, besides a promoter. The term "of the genetic control sequences" is to be understood broadly and means all those sequences which have an effect on the coming into existence, or the function, of the recombinant nucleic acid molecule according to the invention. For example, genetic control sequences modify the transcription and translation in prokaryotic or eukaryotic organisms.

Preferably, the expression cassettes according to the invention comprise a promoter with a specificity as described above 5'-upstream of the respective nucleic acid sequence to be expressed recombinantly, and, as additional genetic control sequence, a terminator sequence in 3'-downstream direction, and, if appropriate, further customary regulatory elements, each operably linked with the nucleic acid sequence to be expressed recombinantly.

Genetic control sequences also comprise further promoters, promoter elements or minimal promoters which are capable of modifying the expression-controlling properties. Thus, for example, the tissue-specific expression can, as a result of genetic control sequences, additionally take place as a function of certain stress factors. Such elements are described, for example, for water stress, abscisic acid (Lam E and Chua N H (1991) J. Biol. Chem. 266(26): 17131-17135) and heat stress (Schoffl F et al. (1989) Mol. Gen. Genet. 217(2-3): 246-53).

In principle, it is possible to use all natural promoters together with their regulatory sequences, such as those mentioned above, for the method according to the invention. Moreover, it is also possible advantageously to use synthetic promoters.

Genetic control sequences furthermore also comprise the 5'-untranslated regions, introns or the noncoding 3' region of genes such as, for example, the actin-1 intron, or the Adh1-S introns 1, 2 and 6 (general: The Maize Handbook, Chapter 116, Freeling and Walbot, Eds., Springer, N.Y. (1994)). It has been demonstrated that these may play a significant role in the regulation of gene expression. Thus, it has been demonstrated that 5'-untranslated sequences are capable of enhancing the transient expression of heterologous genes. An example of translation enhancers which may be mentioned is the 5'-leader sequence from the tobacco mosaic virus (Gallie et al. (1987) Nucl. Acids Res. 15: 8693-8711) and the like. They can furthermore promote tissue specificity (Rouster J et al. (1998) Plant J. 15: 435-440).

The recombinant nucleic acid molecule can advantageously comprise one or more so-called enhancer sequences in operable linkage with the promoter, which sequences make possible an enhanced transgenic expression of the nucleic acid sequence. Additional advantageous sequences may also be inserted at the 3' end of the nucleic acid sequences to be expressed recombinantly, such as further regulatory elements or terminators. The nucleic acid sequences to be expressed recombinantly may be present in the gene construct as one or more copies.

Polyadenylation signals which are suitable as control sequences are plant polyadenylation signals, preferably those which correspond essentially to T-DNA polyadenylation signals from *Agrobacterium tumefaciens*, in particular of gene 3 of the T-DNA (octopine synthase) of the Ti plasmid pTiACHS (Gielen et al. (1984) EMBO J. 3: 835 ff) or functional equivalents thereof. Examples of especially suitable terminator sequences are the OCS (octopine synthase) terminator and the NOS (nopaline synthase) terminator.

Control sequences are furthermore to be understood as meaning those which make possible a homologous recombination or insertion into the genome of the host organism, or which permit the removal from the genome. In the case of homologous recombination, it is possible, for example, to replace the natural promoter of a specific gene with a promoter with specificity for the embryonal epidermis and/or the flower.

A recombinant nucleic acid molecule and a vector derived therefrom may comprise further functional elements. The term functional element is to be understood in a broad sense and means all those elements which have an effect on the generation, multiplication or function of the nucleic acid molecules, vectors or transgenic organisms according to the invention. Examples which may be mentioned, but not by way of limitation, are a) Selection markers which confer a resistance to a metabolism inhibitor such as 2-desoxyglucose 6-phosphate (WO 98/45456), antibiotics or biocides, preferably herbicides, for example kanamycin, G 418, bleomycin, hygromycin or phosphinothricin. Especially preferred selection markers are those which confer a resistance to herbicides. Examples which may be mentioned are: DNA sequences which code for phosphinothricin acetyltransferases (PAT), and inactivate glutamine synthase gene inhibitors (bar and pat gene), 5-enolpyruvylshikimate-3-phosphate synthase genes (EPSP synthase genes) which confer resistance to Glyphosat® (N-(phosphonomethyl)glycine), the gox gene, which codes for Glyphosat®-degrading enzymes (glyphosate oxidoreductase), the deh gene (coding for a dehalogenase which inactivates dalapon), sulfonylurea- and imidazolinone-inactivating acetolactate synthases and bxn genes which code for bromoxynil-degrading nitrilase enzymes, the aasa gene, which confers a resistance to the antibiotic spectinomycin, the streptomycin phosphotransferase (SPT) gene, which confers a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation).

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn and Groskreutz (1999) Mol. Biotechnol. 13(1): 29-44) such as the green fluorescence protein (GFP) (Sheen et al. (1995) Plant Journal 8(5): 777-784; Haselhoff et al. (1997) Proc. Natl. Acad. Sci. USA 94(6): 2122-2127; Reichel et al. (1996) Proc. Natl. Acad. Sci. USA 93(12): 5888-5893; Tian et al. (1997) Plant Cell Rep. 16: 267-271; WO 97/41228; Chui et al. (1996) Curr Biol 6: 325-330; Leffel et al. (1997) Biotechniques. 23(5): 912-8), the chloramphenicoltransferase, a luciferase (Ow et al. (1986) Science 234: 856-859; Millar et al. (1992) Plant. Mol. Biol. Rep. 10: 324-414), the aequorin gene (Prasher et al. (11985) Biochem. Biophys. Res. Commun. 126(3): 1259-1268), the β-galactosidase, R-locus gene (codes for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposiun, 11: 263-282, (1988), with β-glucuronidase being very especially preferred (Jefferson et al., EMBO J. 1987, 6, 3901-3907).

c) Origins of replication which ensure multiplication of the expression cassettes or vectors according to the invention in, for example, *E. coli*. Examples which may be mentioned are ORI (origin of DNA replication), the pBR322 ori or the P15A ori (Sambrook and Russell, see above).

d) Elements which are necessary for *agrobacterium*-mediated plant transformation, such as, for example, the right or left border of the T-DNA or the vir region.

To successfully select transformed cells, it is generally additionally required to introduce a selectable marker which confers a resistance to a biocide (for example a herbicide) to the successfully transformed cells, a metabolism inhibitor such as 2-deoxyglucose 6-phosphate (WO 98/45456) or an antibiotic, thereby permitting the selection of the transformed cells from untransformed cells (McCormick et al. (1986) Plant Cell Reports 5: 81-84).

The present invention furthermore relates to transgenic plant cells and transgenic plants which comprise a nucleic acid sequence according to the invention or a recombinant nucleic acid molecule according to the invention, and parts of the plants, transgenic crop products and transgenic propagation material of these plants, such as protoplasts, plant cells, calli, seeds, tubers, cuttings, and the transgenic progeny of this plant.

The plants are preferably those which belong to the family Poaceae, plants are especially preferably selected from among the plant genera *Hordeum, Avena, Secale, Triticum, Sorghum, Zea, Saccharum* and *Oryza*, very especially preferably plants are selected from among the genera *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugarcane) and *Oryza sativa* (rice).

However, the method according to the present invention is also suitable for dicotyledonous useful plants such as, for example, cotton, leguminoses such as pulses and in particular alfalfa, soybean, oil seed rape, tomato, sugar beet, potato, sunflower, ornamentals and trees. Further useful plants may be fruit (in particular apples, pears, cherries, grapes, citrus, pineapples and bananas), oil palms, tea bushes, cocoa bushes and coffee bushes, tobacco, sisal and, among medicinal plants, Rauwolfia and Digitalis. Especially preferred are the dicotyledonous plants sugar beet, oilseed rape, soybean, tomato, potato and tobacco. Further useful plants can be seen from the U.S. Pat. No. 6,137,030.

The specific expression of the protein according to the invention in the plants according to the invention or in the plant cells according to the invention can be detected, and monitored, with the aid of traditional methods of molecular biology and biochemistry. The skilled worker is familiar with these techniques, and he is easily capable of selecting a suitable detection method, for example a Northern Blot analysis for detecting protein-specific RNA or for determining the accumulation level of protein-specific RNA, or a Southern Blot analysis or PCR analysis for detecting DNA sequences which code for a protein according to the invention. The probe or primer sequences used for this purpose can either be identical to the sequence shown in SEQ ID No. 1 or can feature a small number of deviations from this sequence.

Naturally, the method according to the invention can also be combined with other methods for increasing the pathogen resistance in transgenic plants. Thus, for example, it is possible to increase, by suitable methods, the polypeptide quantity, the activity or the function of one or more resistance factors selected from the group consisting of Bax inhibitor 1 protein from *Hordeum vulgare* (GenBank Acc.-No.: AJ290421), from *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc et al. (2003) Planta 216: 377-386), ROR2 (for example from barley (GenBank Acc.-No.: AY246906)), SnAP34 (for example from barley (GenBank Acc.-No.: AY247208)) and/or lumenal binding protein BiP for example from rice (GenBank Acc.-No. AF006825). Equally, it is possible to reduce, by suitable methods, the polypeptide quantity, the activity or the function of one or more resistance factors selected from the group consisting of RacB (for example from barley (GenBank Acc.-No.: AJ344223)), CSL1 (for example from *Arabidopsis* (GenBank Acc.-No.: NM116593)), HvNaOX (for example from barley (GenBank Acc.-No.: AJ251717); EP 1 525 315), MLO (for example from barley (GenBank Acc.-No. Z83834); WO 98/04586, WO 00/01722, WO 99/47552), ARM1 (armadillo repeat protein; EP application number 05110468.5).

A further subject of the invention relates to the use of the transgenic organisms according to the invention and of the cells, cell cultures, parts—such as, for example, in the case of transgenic plant organisms, roots, leaves and the like—, and transgenic propagation material such as seeds or fruits for the preparation of foodstuffs or feeding stuffs, pharmaceuticals or fine chemicals.

In one embodiment, the invention furthermore relates to a process for the recombinant production of pharmaceuticals or fine chemicals in host organisms, where a host organism or a part thereof is transformed with one of the above-described recombinant nucleic acid molecules, and this nucleic acid molecule comprises one or more structural genes which code for the desired fine chemical or which catalyze the biosynthesis of the desired fine chemical, the transformed host organism is cultured, and the desired fine chemical is isolated from the culture medium. This process can be applied broadly to fine chemicals such as enzymes, vitamins, amino acids, sugars, fatty acids, natural and synthetic flavorings, aroma substances and colorants. The production of tocopherols and tocotrienols and of carotenoids is especially preferred. Culturing the transformed host organisms and isolation from the host organisms, or from the culture medium, is carried out by processes known to the skilled worker. The production of pharmaceuticals such as, for example, antibodies or vaccines, is described in Hood and Jilka (1999). Curr. Opin. Biotechnol. 10(4): 382-6; Ma and Vine (1999) Curr. Top. Microbiol. Immunol. 236: 275-92.

The identification of the leucine-rich-repeat-comprising proteins with a kinase domain, RNR8, from barley as gene which confers barley's resistance to *Blumeria gramninis* isolates, and its use for conferring the pathogen resistance in transgenic plants or plant cells, will now be shown in what follows. The examples hereinbelow are not to be construed as limiting. The content of all of the references, patent applications, patents and published patent applications is incorporated here by way of reference.

EXAMPLES

Example 1

General Cloning Methods

The cloning methods such as, for example, restriction cleavages, agarose gel electrophoresis, purification of DNA fragments, transfer of nucleic acids onto nitrocellulose and nylon membranes, linking of DNA fragments, transformation of *E. coli* cells, the culturing of bacteria and the sequence analysis of recombinant DNA were carried out as described by Sambrook et al. (2001), see above.

Example 2

Sequence Analysis of Recombinant DNA

The sequencing of recombinant DNA molecules was carried out using a laser fluorescence DNA sequencer, from ABI, following the method of Sanger (Sanger et al. (1977) Proc. Natl. Acad. Sci. USA 74: 5463-5467).

Example 3

BAC Screening for Identifying the Clone which Comprises the Sequence According to the Invention DNA pools from a barley BAC library (Yu et. al. (2000) TAG 101: 1093-99) were used for identifying the gene coding for the sequence according to the invention in barley. BAC clones which comprise the sequence according to the invention were identified by means of PCR using the primers 5' CTT TCG TGC TTA TGT GGG TGT GAC (SEQ ID NO: 4) and 5' CAT GAG GAG TCT GCA ATA AGG A (SEQ ID NO: 5).

The PCR method was chosen for its high sensitivity to detect the searched-for DNA sequence. The analysis was carried out in a reaction volume of 20 µl. The reaction mixture consisted of 10 mM Tris-HCl, pH 9.0; 50 mM KCl; 0.1% Triton X-100, 0.2 mM dNTP; 2 mM $MgCl_2$, in each case 0.6 µM oligonucleotides and Taq polymerase (concentration in the reaction mixture: ~1 U $µl^{-1}$). Either 10 ng of BAC pool DNA or 2 µl of bacterial culture (for colony PCR) were used per reaction mixture. Existing cDNA sequences served as the basis for deriving the oligonucleotides 5'GGA TTT GTC ACG TCC AAC CT (SEQ ID NO: 6) and 5'ATT GGC AAT TGT GAT AGC CC (SEQ ID NO: 7).

The BAC DNA to be amplified and the primers were initially introduced, and subsequently mixed with the PCR reaction mixture. To destroy and disrupt the bacteria in a colony PCR, the initially introduced mixture was heated for 5 min at 95° C. before adding the PCR reaction mixture. An initial step of 5 min at 95° C. was used for denaturing the double-stranded DNA.

The touch-down PCR reaction was carried out in the steps 30 s 95° C.; 30 s 60 to 55° C. and 60 s 72° C. for the first 10 cycles. With each cycle, the temperature was reduced by 0.5° C. (60 to 55° C.). A further 30 cycles were carried out with the steps 30 s 95° C.; 30 s 55° C. and 60 s 72° C. To carry out the final chain elongation, the reaction was incubated for 5 min at 72° C. before being cooled to, and kept constant at, a temperature of 20° C. Since it was expected that, at 189 bp, the reaction product was short, the PCR experiments were analyzed using 2.5% agarose gels in 0.5×TBE buffer.

Identified individual clones were subcloned in two steps for identifying gene and promoter. First, the BAC DNA of a single clone was isolated by means of a Qiagen column (Maxi-Kit; Qiagen; isolation in accordance with the manufacturer's protocol). 5-10 kbp fragments were generated from this BAC DNA by means of shearing (Hydroshear: Genomic Solutions), and the resulting ends were filled up with Klenow to give smooth ends (reaction as specified in the manufacturer's protocol). The selection of the fragment lengths was carried out using an 0.8% agarose gel in 0.5% TBE. The relevant fragment length range was excised from the gel, and the DNA was eluted from the agarose gel with the aid of the Qiagen Gel Extraction Kit (elution in accordance with the manufacturer's protocol). The eluted 5-10 kbp fragments were ligated into an EcoRV-linearized pbluescript II SK(−) vector with smooth dephosphorylated ends (restriction and dephosphorylation in accordance with the manufacturer's instructions) and transformed chemically/thermally into highly competent *E. coli* cells. Thereafter, the transformants were arranged randomly with the aid of a picking robot (Qpick, Genetix) and transferred into microtiter plates with LB medium.

Using PCR, the subfragment which comprises the gene of interest and which maximizes the length of the potential 5'-upstream region was selected by means of PCR. The selected subfragment was again sheared into 1-2 kbp fragments, ligated, transformed, and the clones were stored in microtiter plates (see above). Among the picked clones, 96 colonies were selected at random and sequenced using the TempliPhi protocol, in accordance with the manufacturer's protocol. The sequences were assembled. The sequence information obtained was used for annotating the coding exons in comparison with known sequences of other organisms in order to determine the sequence according to the invention and its potential promoters.

Example 4

Subcloning of the RNR8 Gene into pIPKTA9

In order to verify in greater detail whether the identified gene RNR8 is responsible for mediating pathogen resistance, this gene was subcloned into the vector pIPKTA9 using the following protocol:
1. Digestion of NBS-LRR BAC (No. 027N11) with Psp 1406 I and XmaJI. This excises almost the entire coding portion of the RNR8 gene.
2. Blunt-ending with Klenow.
3. Gel elution of the 11 kb band of step 2 using the Qiagen gel extraction kit.
4. Ligation of the 11 kb band NBS_LRR (step 3) into TA38 in the presence of Swa I (Douchkov et al. (2005) Molecular Plant-Microbe Interactions 18: 755-761.)
5. PCR of a 1 kb NBS-LRR fragment in order to complete the coding region of the gene at the 5' end (upstream). Thermal Ace Polymerase (produces blunt-ended fragments).

```
                                          (SEQ ID NO: 8)
Primer NBS-LRR E1: GCT GAA CCA ACC CGG GGA GAA ATA (SEQ ID NO: 9)
Primer NBS-LRR F1: AGA TGA TCG GAA GAA CAG TGC AAC
```

6. PCR purification (step 5) with MinElute plates.
7. Cloning of the 5' NBS-LRR PCR fragment (step 6) into pIPKTA9, cleaved by Sma I.
8. Digestion of the 11 kb LRR in TA38 (step 4) with Aar I and Not I.
9. Gel elution of the 11 kb LRR of step 8.
10. Digestion of pIPKTA9_NBS_LRR_5' (step 7) with Aar I and Not I.
11. Gel elution ~3.5 kb vector band of step 10.
12. Ligation of the fragments of steps 7 and 11 with T4 DNA ligase (Fermentas).
13. Verification of the final construct pIPKTA9_NBS-LRR by sequencing.

Since the same effects were obtained with the construct pIPKTA9_NBS-LRR as with the BAC clone, it was concluded that RNR8 is the gene on BAC No. 027N11 which is responsible for the observed pathogen resistance (see, in this context, also FIG. 1).

Example 5

Transient Expression in Wheat by Particle Bombardment

The following construct mixture was introduced into wheat leaves using a gene gun (Bio-Rad, model PDS-1000/He, Hepta adapter) by means of biolistic transformation, following the method of Douchkov et al. (2005) Mol. Plant-Microbe Interact. 18: 755-761:

| Plasmid | Reaction 1 | Reaction 2 | Reaction 3 | Reaction 4 |
|---|---|---|---|---|
| pUbiGUS (reporter gene construct) | 7 µg/shot | 7 µg/shot | 7 µg/shot | 7 µg/shot |
| pIPKTA9 (empty overexpression vector) | 7 µg/shot | — | — | — |
| pIPKTA9_TaPERO | — | — | 7 µg/shot | — |
| BAC 027N11 | — | 14 µg/shot | — | — |
| pIPKTA9_NBS LRR | — | — | — | 7 µg/shot |

For the DNA coating, 2.18 mg of gold particles (diameter 1.0 µm, particle density 25 mg ml$^{-1}$ in 50% (v/v) glycerol) were mixed with 14-21 µg of "supercoiled" DNA for each shot, and treated with 1 M Ca(NO$_3$)$_2$ pH 10 in such a way that the final Ca(NO$_3$)$_2$ concentration was 0.5 M. After centrifuging and washing with 70% (v/v) ethanol, the particles were resuspended in 96% (v/v) ethanol and divided between the 7 macrocarriers. In a vacuum (3.6×10$^3$ Pa), the particles were introduced into in each case 7 leaf segments of 7-day-old wheat plants (variety Kanzler) by means of a helium pressure surge of 7.6×10$^6$ Pa. For the bombardment, the leaf segments were placed into a Petri dish on 0.5% (w/v) Phytoagar which had been treated with 20 µg ml$^{-1}$ benzimidazole. The leaves were subsequently incubated for 4 h at +20° C. and in indirect daylight.

Example 6

Inoculation of the Leaf Segments

The bombarded leaves were transferred onto 1% (w/v) Phytoagar with 20 µg ml$^{-1}$ benzimidazole in 20×20 cm polycarbonate dishes. The infection with wheat powdery mildew spores was carried out in an inoculation tower by shaking spores from severely infected wheat leaves into the tower. The inoculum density was around 200 spores/mm$^2$. After 5 min, the dishes were removed, sealed and incubated for 40-48 h at +20° C. and in indirect daylight.

Example 7

Histochemical GUS Detection

The leaves were infiltrated in vacuo with the GUS detection solution (10 mM EDTA, 1.4 mM K$_3$[Fe(CN)$_6$], 1.4 mM K$_4$[Fe(CN)$_6$], 0.1% (v/v) Triton X-100, 20% (v/v) methanol, 1 mg/ml 3-bromo-4-chloro-3-indolyl-β-D-glucuronic acid, 100 mM sodium phosphate buffer, pH 7.0) and incubated overnight at +37° C. After the detection solution had been removed, the leaves were destained for 15 min at +20° C. in a solution of 7.5% (w/v) trichloroacetic acid and 50% (v/v) methanol.

Light microscopy was carried out using a Zeiss Axiolab microscope at 200× magnification. The cell contents of cells with GUS expression are blue. Using quantitative microscopy, the number of GUS-stained cells and the number of GUS-stained cells which contain at least 1 haustorium of the wheat powdery mildew fungus were counted for each shot. The susceptibility index was calculated from the number of haustorium-containing GUS-positive cells/all GUS-positive cells.

The result of the inoculation experiment is shown in FIG. 1. It emerged that the expression of the protein according to the invention from the BAC clone or the expression vector pIPKTA9_NBS-LRR reduces the susceptibility of the wheat plants to wheat powdery mildew by approximately 50% in comparison with plants which have been transformed with the empty vector.

FIGURES

FIG. 1: Transient complementation experiment in wheat with barley BAC clone 027N11 (Morex BAC library) which comprises the leucine-rich-repeat protein kinase Rnr8. Wheat leaves were co-bombarded with pUbiGUS and either pIPKTA9 (empty overexpression vector), BAC clone 027N11, pIPKTA9_NBS LRR (see example 4) or pIPKTA9:TaPERO (overexpression construct for a peroxidase as a positive control). The data shown are means and standard deviations from 2 individual experiments with in each case 2 parallel bombardments.

The invention claimed is:

1. An isolated nucleic acid molecule, comprising a nucleic acid sequence selected from the group consisting of:
   i) a nucleic acid sequence comprising a nucleotide sequence which comprises the coding sequence of SEQ ID NO: 1,
   ii) a nucleic acid sequence comprising a nucleotide sequence which codes for a protein with the amino acid sequence shown in SEQ ID NO: 2,
   iii) a nucleic acid sequence comprising a nucleotide sequence which has at least 96% sequence identity with the coding sequence of SEQ ID NO: 1, and
   iv) a nucleic acid sequence comprising a nucleotide sequence which, under high stringent conditions comprising a wash step of 0.2×SSC at 65° C., hybridizes with a complementary strand of the nucleotide sequence of i) to iii),
   which codes for a protein which confers an increased fungal pathogen resistance in plants.

2. The nucleic acid molecule of claim 1, where the nucleic acid sequence originates from Hordeum vulgare.

3. A recombinant protein which confers, in plants, an increased fungal pathogen resistance, and which is encoded by the nucleic acid sequence of claim 1.

4. A recombinant nucleic acid molecule, comprising the following elements in 5'-3' orientation:
   regulatory sequences of a promoter which is active in plant cells,
   the nucleic acid sequence of claim 1 in operable linkage thereto,
   optionally, regulatory sequences which may act as transcription, termination and/or polyadenylation signals in the plant cell, in operable linkage thereto.

5. The recombinant nucleic acid molecule of claim 4, wherein the nucleic acid sequence is expressed under the control of a constitutive promoter.

6. The recombinant nucleic acid molecule of claim 4, wherein the nucleic acid sequence is expressed under the control of a tissue-specific promoter.

7. The recombinant nucleic acid molecule of claim 6, wherein the tissue-specific promoter is an epidermis-, mesophyll- or leaf-specific promoter.

8. The recombinant nucleic acid molecule of claim 4, wherein the nucleic acid sequence is expressed under the control of an inducible promoter.

9. The recombinant nucleic acid molecule of claim 8, wherein the inducible promoter is a pathogen- or wound-inducible promoter.

10. A method of increasing fungal pathogen resistance in transgenic plants, comprising:
   introducing and expressing the nucleic acid sequence of claim 1 in a plant or plant cell; and
   selecting a plant having increased fungal pathogen resistance.

11. A method of increasing fungal pathogen resistance in transgenic plants comprising
   a) generating the recombinant nucleic acid molecule of claim 4,
   b) transferring the recombinant nucleic acid molecule from a) into a plant cell,
   c) regenerating a plant from the transformed plant cell; and
   d) selecting a plant having increased fungal pathogen resistance.

12. The method of claim 10, where the fungal pathogen is a selected from the group consisting of mildew, rust, *Fusarium*, and *Septoria* fungi.

13. A transgenic plant cell, comprising the nucleic acid sequence of claim 1 or a recombinant nucleic acid molecule comprising in 5'-3' orientation regulatory sequences of a promoter which is active in plant cells and the nucleic acid sequence of claim 1 in operable linkage thereto.

14. The transgenic plant cell of claim 13, which comprises an increased content of a protein encoded by the nucleic acid sequence in comparison with a wild-type cell.

15. The transgenic plant cell of claim 13, which features a fungal pathogen resistance which is increased in comparison with a wild-type cell.

16. The transgenic plant cell of claim 13, which features an increased resistance to mildew, rust and/or *Septoria* fungi.

17. The transgenic plant cell of claim 16, which features an increased resistance to Formae speciales of mildew.

18. A transgenic plant, comprising the plant cell of claim 13, and parts of the plant, transgenic crop products, and transgenic propagation material of the plant, and the transgenic progeny of this plant.

19. The transgenic plant of claim 18, wherein the transgenic plant is a monocotyledonous plant.

20. The transgenic plant of claim 18, wherein the transgenic plant is a dicotyledonous plant.

21. The recombinant nucleic acid molecule of claim 5, wherein the promoter is the 35S CaMV promoter or ubiquitin promoter.

22. The transgenic plant of claim 19, wherein the monocotyledonous plant belongs to the genera *Avena, Triticum, Secale, Hordeum, Oryza, Panicum, Pennisetum, Setaria, Sorghum,* or *Zea*.

23. The transgenic plant of claim 20, wherein the dicotyledonous plant is cotton, a legume, a pulse, alfalfa, soybean, oilseed rape, canola, tomato, sugar beet, potato, an ornamental, sunflower, tobacco, or a tree.

24. A transgenic plant generated by the method of claim 10, and parts of the plant, transgenic crop products, and transgenic propagation material of the plant, and the transgenic progeny of this plant.

25. The method of claim 11, wherein the recombinant nucleic acid molecule is integrated into the plant genome.

* * * * *

UNITED STATES PATENT AND TRADEMARK OFFICE
CERTIFICATE OF CORRECTION

PATENT NO.         : 8,222,486 B2                                  Page 1 of 1
APPLICATION NO.    : 12/438766
DATED              : July 17, 2012
INVENTOR(S)        : Dimitar Douchkov et al.

It is certified that error appears in the above-identified patent and that said Letters Patent is hereby corrected as shown below:

In the Claims:

Claim 10, in column 44, on line 63, "introducing and expressing the nucleic acid sequence of" should read -- a) introducing and expressing the nucleic acid sequence of --

Claim 10, in column 44, on line 66, "selecting a plant having increased fungal pathogen resis-" should read -- b) selecting a plant having increased fungal pathogen resis- --

Claim 12, in column 45, on line 11, "a selected from the the group consisting of mildew, rust," should read -- selected from the group consisting of mildew, rust, --

Signed and Sealed this
Thirtieth Day of April, 2013

Teresa Stanek Rea
*Acting Director of the United States Patent and Trademark Office*